United States Patent
Shah

(10) Patent No.: US 11,710,576 B2
(45) Date of Patent: Jul. 25, 2023

(54) METHOD AND SYSTEM FOR COMPUTER-AIDED ESCALATION IN A DIGITAL HEALTH PLATFORM

(71) Applicant: OrangeDot, Inc., Santa Monica, CA (US)

(72) Inventor: Setu Shah, Santa Monica, CA (US)

(73) Assignee: OrangeDot, Inc., Santa Monica, CA (US)

( * ) Notice: Subject to any disclaimer, the term of this patent is extended or adjusted under 35 U.S.C. 154(b) by 0 days.

(21) Appl. No.: 17/752,097

(22) Filed: May 24, 2022

(65) Prior Publication Data

US 2022/0375627 A1 Nov. 24, 2022

Related U.S. Application Data

(60) Provisional application No. 63/192,413, filed on May 24, 2021.

(51) Int. Cl.
*G16H 80/00* (2018.01)
*G16H 50/20* (2018.01)
(Continued)

(52) U.S. Cl.
CPC ........... *G16H 80/00* (2018.01); *G06F 40/109* (2020.01); *G06F 40/166* (2020.01); *G06F 40/205* (2020.01); *G06F 40/237* (2020.01); *G06F 40/253* (2020.01); *G06F 40/279* (2020.01); *G06F 40/30* (2020.01); *G06F 40/55* (2020.01); *G06N 20/00* (2019.01); *G16H 50/20* (2018.01); *G16H 50/30* (2018.01)

(58) Field of Classification Search
CPC ........ G16H 10/00–80/00; G06N 3/00–99/007; G06F 1/00–2221/2153
See application file for complete search history.

(56) References Cited

U.S. PATENT DOCUMENTS 4,845,323 A 7/1989 Beggs
6,356,940 B1 3/2002 Short
(Continued)

FOREIGN PATENT DOCUMENTS

CN 101600008 A 12/2009
DE 102016101665 A1 * 8/2016 ....... G06F 16/24578
(Continued)

OTHER PUBLICATIONS

Calvo et al., "Natural language processing in mental health applications using non-clinical texts," Natural Language Engineering 23(5): 649-685. © Cambridge University Press 2017. (Year: 2017).*
(Continued)

*Primary Examiner* — Jonathon A. Szumny
(74) *Attorney, Agent, or Firm* — Jeffrey Schox; Caitlin Ploch

(57) ABSTRACT

A system for computer-aided escalation can include and/or interface with any or all of: a set of user interfaces (equivalently referred to herein as dashboards and/or hubs), a computing system, and a set of models. A method for computer-aided escalation includes any or all of: receiving a set of inputs; and processing the set of inputs to determine a set of outputs; triggering an action based on the set of outputs; and/or any other processes.

18 Claims, 11 Drawing Sheets

(51) Int. Cl.

| | | |
|---|---|---|
| G16H 50/30 | (2018.01) | |
| G06F 40/55 | (2020.01) | |
| G06F 40/205 | (2020.01) | |
| G06F 40/109 | (2020.01) | |
| G06F 40/30 | (2020.01) | |
| G06F 40/253 | (2020.01) | |
| G06F 40/279 | (2020.01) | |
| G06F 40/237 | (2020.01) | |
| G06N 20/00 | (2019.01) | |
| G06F 40/166 | (2020.01) | |

(56) References Cited

U.S. PATENT DOCUMENTS

| | | |
|---|---|---|
| 6,827,670 B1 | 12/2004 | Stark et al. |
| 7,188,151 B2 | 3/2007 | Kumar et al. |
| 7,246,677 B2 | 7/2007 | Fredriksson et al. |
| 7,248,677 B2 | 7/2007 | Randall et al. |
| 7,337,158 B2 | 2/2008 | Fratkina et al. |
| 7,376,700 B1 | 5/2008 | Clark et al. |
| 7,395,216 B2 | 7/2008 | Rosenfeld et al. |
| 7,584,166 B2 | 9/2009 | Grichnik |
| 7,761,309 B2 | 7/2010 | Sacco et al. |
| 7,818,185 B2 | 10/2010 | Bjorner et al. |
| 7,912,528 B2 | 3/2011 | Krishnan et al. |
| 7,914,468 B2 | 3/2011 | Shalon et al. |
| 8,160,901 B2 | 4/2012 | Heywood et al. |
| 8,265,955 B2 | 9/2012 | Michelson et al. |
| 8,398,538 B2 | 3/2013 | Dothie et al. |
| 8,423,387 B1 | 4/2013 | Mirza |
| 8,488,761 B2 | 7/2013 | Reding et al. |
| 8,500,635 B2 | 8/2013 | Zilca et al. |
| 8,622,900 B2 | 1/2014 | Jain et al. |
| 8,655,817 B2 | 2/2014 | Hasey et al. |
| 8,684,922 B2 | 4/2014 | Tran |
| 8,726,195 B2 | 5/2014 | Bill |
| 8,781,102 B2 | 7/2014 | Conway et al. |
| 8,977,248 B1 | 3/2015 | Bladon et al. |
| 9,019,106 B2 | 4/2015 | Alameh et al. |
| 9,116,669 B2 | 8/2015 | Desai et al. |
| 9,195,948 B2 | 11/2015 | Son et al. |
| 9,286,442 B2 | 3/2016 | Csoma et al. |
| 9,294,403 B2 | 3/2016 | Mejia et al. |
| 9,497,585 B1 * | 11/2016 | Cooley .................. H04W 4/029 |
| 9,684,922 B2 | 6/2017 | Elberbaum |
| 9,713,724 B2 | 7/2017 | Petersen et al. |
| 9,754,220 B1 * | 9/2017 | Brestoff ............... G06N 3/0445 |
| 9,763,592 B2 | 9/2017 | Le et al. |
| 2002/0198473 A1 | 12/2002 | Kumar et al. |
| 2003/0119794 A1 | 6/2003 | Bacaner et al. |
| 2004/0078223 A1 | 4/2004 | Sacco et al. |
| 2004/0122702 A1 | 6/2004 | Sabol et al. |
| 2004/0122703 A1 | 6/2004 | Walker et al. |
| 2004/0143453 A1 | 7/2004 | Weaver |
| 2004/0199401 A1 | 10/2004 | Wagner et al. |
| 2004/0225340 A1 | 11/2004 | Evans |
| 2005/0020903 A1 | 1/2005 | Krishnan et al. |
| 2005/0055321 A1 | 3/2005 | Fratkina et al. |
| 2005/0069936 A1 | 3/2005 | Diamond et al. |
| 2005/0108051 A1 | 5/2005 | Weinstein |
| 2005/0169446 A1 | 8/2005 | Randall et al. |
| 2006/0064037 A1 | 3/2006 | Shalon et al. |
| 2007/0022612 A1 | 2/2007 | Perrin |
| 2007/0094048 A1 | 4/2007 | Grichnik |
| 2007/0226012 A1 | 9/2007 | Salgado et al. |
| 2007/0288266 A1 | 12/2007 | Sysko et al. |
| 2008/0059570 A1 | 3/2008 | Bill |
| 2008/0061125 A1 | 3/2008 | Langlois et al. |
| 2008/0201429 A1 | 8/2008 | Barbell et al. |
| 2009/0125333 A1 | 5/2009 | Heywood et al. |
| 2009/0161907 A1 | 6/2009 | Healey et al. |
| 2009/0247834 A1 | 10/2009 | Schechter |
| 2009/0254971 A1 | 10/2009 | Herz et al. |
| 2010/0082367 A1 | 4/2010 | Hains et al. |
| 2010/0179833 A1 | 7/2010 | Roizen et al. |
| 2010/0198614 A1 | 8/2010 | Chopra et al. |
| 2010/0203876 A1 | 8/2010 | Krishnaswamy |
| 2010/0280838 A1 | 11/2010 | Bosworth et al. |
| 2010/0325588 A1 | 12/2010 | Reddy et al. |
| 2011/0009715 A1 | 1/2011 | O'Reilly et al. |
| 2011/0015467 A1 | 1/2011 | Dothie et al. |
| 2011/0066036 A1 | 3/2011 | Zilca et al. |
| 2011/0082712 A1 | 4/2011 | Eberhardt et al. |
| 2011/0118555 A1 | 5/2011 | Dhumne et al. |
| 2011/0119212 A1 | 5/2011 | De Bruin et al. |
| 2011/0125238 A1 | 5/2011 | Nofzinger |
| 2011/0161110 A1 | 6/2011 | Mault |
| 2011/0184250 A1 | 7/2011 | Schmidt et al. |
| 2011/0245633 A1 | 10/2011 | Goldberg et al. |
| 2011/0295621 A1 | 12/2011 | Farooq et al. |
| 2011/0306028 A1 | 12/2011 | Galimore |
| 2011/0314558 A1 * | 12/2011 | Song ..................... G06F 21/316 726/28 |
| 2012/0016218 A1 | 1/2012 | Lau et al. |
| 2012/0041786 A1 | 2/2012 | Yu |
| 2012/0053425 A1 | 3/2012 | Michelson et al. |
| 2012/0131183 A1 | 5/2012 | Heidt et al. |
| 2012/0143013 A1 | 6/2012 | Davis et al. |
| 2012/0179480 A1 | 7/2012 | Patel et al. |
| 2012/0203545 A1 * | 8/2012 | Shaw ..................... G10L 17/26 704/9 |
| 2012/0221357 A1 | 8/2012 | Krause et al. |
| 2012/0289791 A1 | 11/2012 | Jain et al. |
| 2013/0004129 A1 | 1/2013 | Zhang |
| 2013/0041290 A1 | 2/2013 | Kording et al. |
| 2013/0042116 A1 | 2/2013 | Sakumoto |
| 2013/0060580 A1 | 3/2013 | Chapman et al. |
| 2013/0085758 A1 | 4/2013 | Csoma et al. |
| 2013/0085773 A1 | 4/2013 | Yao et al. |
| 2013/0095459 A1 | 4/2013 | Tran |
| 2013/0117040 A1 | 5/2013 | James et al. |
| 2013/0154838 A1 | 6/2013 | Alameh et al. |
| 2013/0179178 A1 | 7/2013 | Vemireddy et al. |
| 2013/0246330 A1 | 9/2013 | Son et al. |
| 2013/0297536 A1 | 11/2013 | Almosni et al. |
| 2013/0324861 A1 | 12/2013 | Ando et al. |
| 2014/0019161 A1 | 1/2014 | Op Den Buijs et al. |
| 2014/0039907 A1 | 2/2014 | Schaefer et al. |
| 2014/0039914 A1 | 2/2014 | Dansereau et al. |
| 2014/0052465 A1 | 2/2014 | Madan et al. |
| 2014/0052474 A1 | 2/2014 | Madan et al. |
| 2014/0257439 A1 | 9/2014 | Douglas |
| 2015/0003247 A1 | 1/2015 | Mejia et al. |
| 2015/0187199 A1 | 7/2015 | Chang et al. |
| 2015/0310606 A1 | 10/2015 | Shreve et al. |
| 2015/0370994 A1 | 12/2015 | Madan et al. |
| 2016/0292862 A1 | 10/2016 | Mask |
| 2016/0317781 A1 | 11/2016 | Proud |
| 2017/0124643 A1 | 5/2017 | Haimi et al. |
| 2018/0089449 A1 * | 3/2018 | Boudreau ........... H04L 63/0227 |
| 2018/0342326 A1 | 11/2018 | Moturu et al. |
| 2018/0374046 A1 | 12/2018 | Powers et al. |
| 2019/0042699 A1 * | 2/2019 | Bastide .................. G16H 80/00 |
| 2020/0242566 A1 * | 7/2020 | Agarwal ........... G06Q 10/1095 |
| 2021/0390625 A1 * | 12/2021 | Hayes ................ G06Q 30/0185 |
| 2022/0061746 A1 * | 3/2022 | Lyman .................. G16H 30/40 |

FOREIGN PATENT DOCUMENTS

| | | |
|---|---|---|
| JP | 2003339674 | 12/2003 |
| JP | 2010514497 A | 5/2010 |
| WO | 02067122 A1 | 8/2002 |
| WO | 2008085308 A1 | 7/2008 |
| WO | 2008096634 A1 | 8/2008 |
| WO | 2012025622 A2 | 3/2012 |
| WO | 2013042116 A1 | 3/2013 |
| WO | 2015003247 A1 | 1/2015 |

OTHER PUBLICATIONS

Coppersmith et al., "Natural Language Processing of Social Media as Screening for Suicide Risk," Biomedical Informatics Insights vol. 10: 1-11 © The Author(s) 2018. (Year: 2018).*

(56) References Cited

OTHER PUBLICATIONS

Ji et al., "Supervised Learning for Suicidal Ideation Detection in Online User Content," Hindawi Complexity vol. 2018, Article ID 6157249, 10 pages https://doi.org/10.1155/2018/6157249. (Year: 2018).*

Skaik et al., "Using Social Media for Mental Health Surveillance: A Review," ACM Comput. Surv. 53, 6, Article 129 (Dec. 2020), 31 pages, https://doi.org/10.1145/3422824. (Year: 2020).*

"Pitzer, Patient Health Questionnaire (PH-9)", Pfizer Non-Patent Literature, 1999, pp. 1 and 2.

Major Smith, Virginia, et al., "Work Time Interference With Family, and Psychological Distress", 2002, Journal of Applied Psychology, vol. 87, No. 3, 427-436 (Year: 2002)., Feb. 21, 2018 00:00:00.0.

Thomee, Sara, et al., "Mobile phone use and stress, sleep disturbances, and symptoms of depression among young adults—a prospective short study", BMC Public Health, Biomed Central, London, GB, vol. 11, No. 1, Jan. 31, 2011, p. 66.

Yen, Cheng-Fang, et al., "Symptoms of problematic cellular phone use, functional impairment and its association with depression among adolescents in Southern Taiwan", Journal of Adolescence, Academic Press, Amsterdam, NL, vol. 32, No. 4, Aug. 1, 2009, pp. 863-873.

\* cited by examiner

Workflow for determining a safety risk prediction score (e.g., to predict suicidal ideation)

Workflow for determining a clinical escalation prediction score (e.g., to predict if a user should be escalated to clinical care)

METHOD AND SYSTEM FOR COMPUTER-AIDED ESCALATION IN A DIGITAL HEALTH PLATFORM

CROSS-REFERENCE TO RELATED APPLICATIONS

This application claims the benefit of U.S. Provisional Application No. 63/192,413, filed 24 May 2021, which is incorporated in its entirety by this reference.

TECHNICAL FIELD

This invention relates generally to the digital health field, and more specifically to a new and useful system and method for computer-aided escalation in the digital health field.

BACKGROUND

In recent years, health coaching (e.g., mental health coaching, physical health coaching, etc.) has been enabled in remote settings through remote platforms, such as digital health platforms. While this has had numerous advantages in convenience and accessibility for participants, as these programs scale and as the participants themselves evolve and change, it is a significant and complex challenge to maintain appropriate levels and/or types of care for each of the individuals participating in the platform. This can lead, for instance, in conventional systems and methods, to situations in which certain participants—such as those experiencing a mental health condition—are overlooked or not provided appropriate resources for care in a timely manner, which could have detrimental effects.

Thus, there is a need in the digital health field to create an improved and useful system and method for computer-aided escalation.

DESCRIPTION OF THE PREFERRED EMBODIMENTS

The following description of the preferred embodiments of the invention is not intended to limit the invention to these preferred embodiments, but rather to enable any person skilled in the art to make and use this invention.

1. Overview

Figure 1:
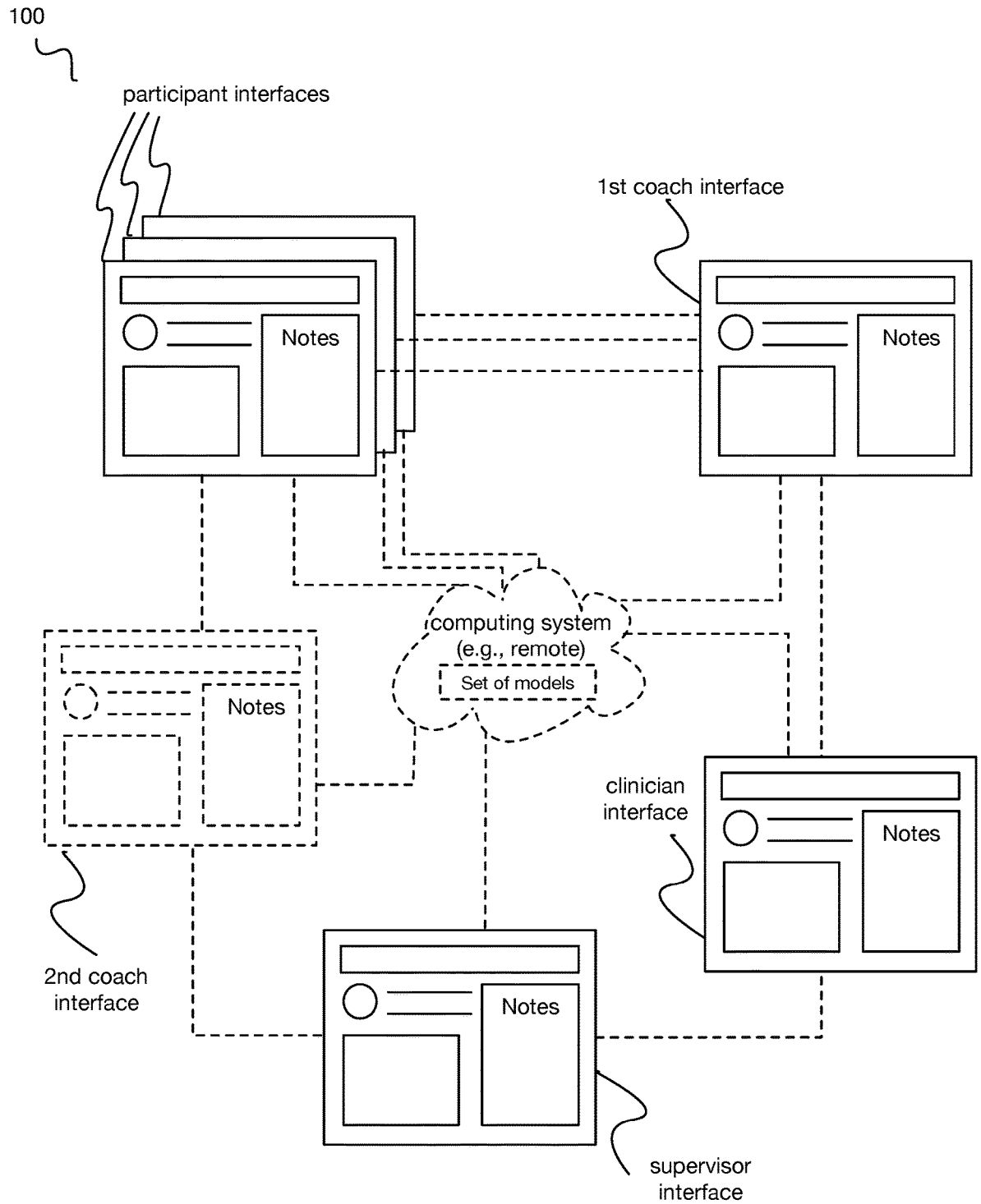
FIG. 1 is a schematic of a system for computer-aided care adjustment in a digital health platform.

As shown in FIG. 1, a system 100 for computer-aided escalation can include and/or interface with any or all of: a set of user interfaces (equivalently referred to herein as dashboards and/or hubs), a computing system, and a set of models. Additionally or alternatively, the system can include and/or interface with any other suitable components. Further additionally or alternatively, the system 100 can include and/or interface with any or all of the systems, components, embodiments, and/or examples described in any or all of: U.S. application Ser. No. 13/969,349, filed 16 Aug. 2013; U.S. application Ser. No. 14/839,053, filed 28 Aug. 2015; U.S. application Ser. No. 14/839,232, filed 28 Aug. 2015; U.S. application Ser. No. 15/005,923, filed 25 Jan. 2016; U.S. application Ser. No. 15/069,163, filed 14 Mar. 2016; U.S. application Ser. No. 17/463,432, filed 31 Aug. 2021; U.S. application Ser. No. 15/482,995, filed 10 Apr. 2017; U.S. application Ser. No. 15/587,599, filed 5 May 2017; and U.S. application Ser. No. 17/401,956, filed 13 Aug. 2021; each of which is incorporated herein in its entirety by this reference.

Figure 2:
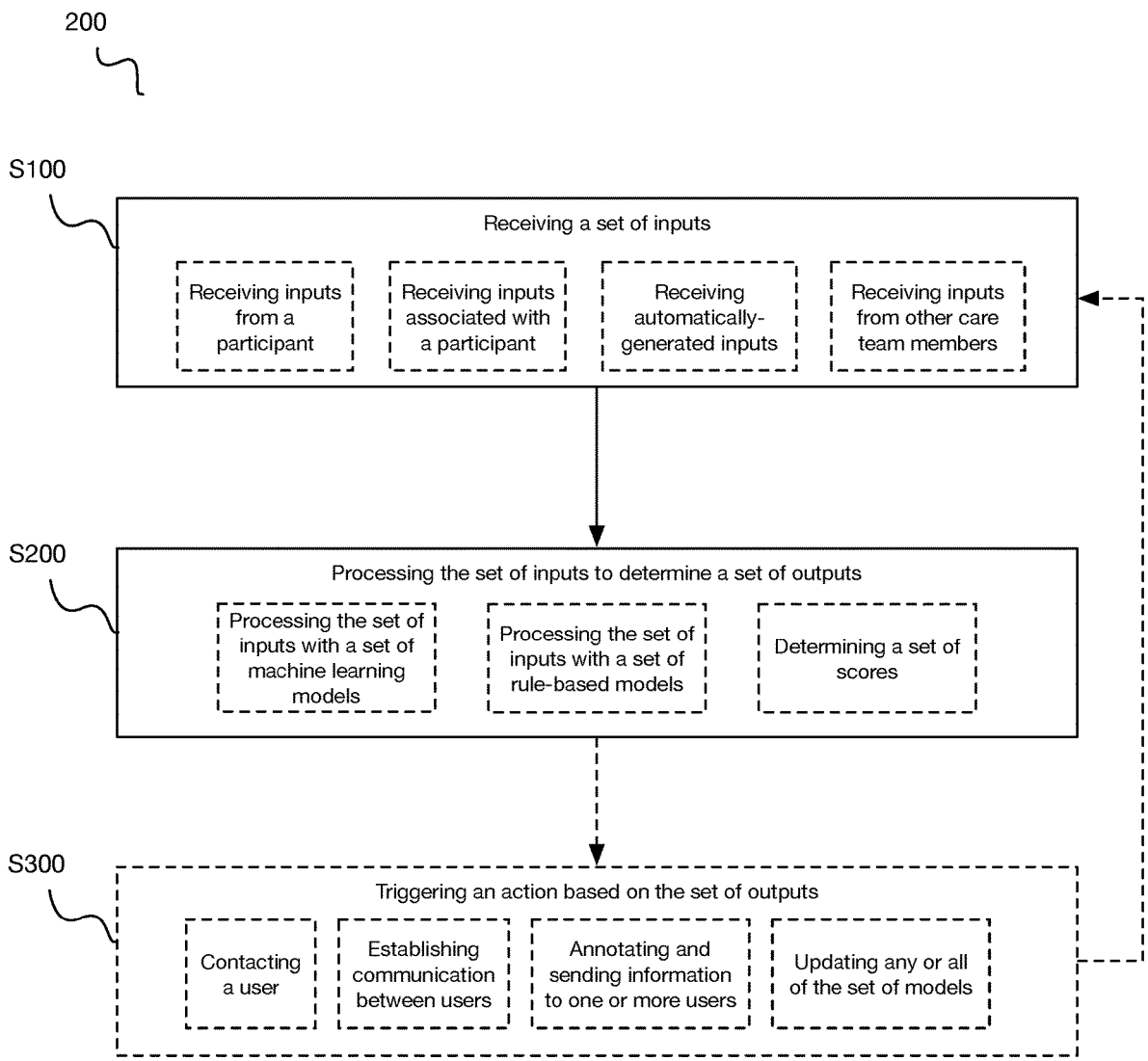
FIG. 2 is a schematic of a method for computer-aided care adjustment in a digital health platform.

As shown in FIG. 2, a method 200 for computer-aided escalation includes receiving a set of inputs S100 and processing the set of inputs to determine a set of outputs S200. Additionally or alternatively, the method 200 can include triggering an action based on the set of outputs S300 and/or any other processes. The method 200 can be performed with a system as described above and/or any other suitable system. Further additionally or alternatively, the method 200 can include and/or interface with any or all of the methods, processes, embodiments, and/or examples described in any or all of: U.S. application Ser. No. 13/969, 349, filed 16 Aug. 2013; U.S. application Ser. No. 14/839, 053, filed 28 Aug. 2015; U.S. application Ser. No. 14/839, 232, filed 28 Aug. 2015; U.S. application Ser. No. 15/005, 923, filed 25 Jan. 2016; U.S. application Ser. No. 15/069, 163, filed 14 Mar. 2016; U.S. application Ser. No. 17/463, 432, filed 31 Aug. 2021; U.S. application Ser. No. 15/482, 995, filed 10 Apr. 2017; U.S. application Ser. No. 15/587, 599, filed 5 May 2017; and U.S. application Ser. No. 17/401,956, filed 13 Aug. 2021; each of which is incorporated herein in its entirety by this reference.

2. Benefits

The system and method for computer-aided escalation in a digital platform can confer several benefits over current systems and methods.

In a first set of variations, the technology confers the benefit of automatically detecting that a participant in a digital platform should be escalated to a higher level of care, such as to care involving a clinician (e.g., therapist, psychiatrist, etc.) in addition to and/or rather than a non-clinical coach, to a higher tier of care in the digital platform, and/or otherwise escalated to another type, associated features, and/or timeline of care. Additionally or alternatively, the technology can confer the benefit of automatically detecting that a participant is ready and/or suitable for de-escalation (e.g., once a participant has improved in his or her mental health condition, once a participant is no longer experiencing suicidal ideation, etc.). The technology can further optionally confer the benefit of automating any or all of a set of actions performed in response to detecting that the participant should be escalated and/or de-escalated (e.g., automatically transmitting a notification to a coach and/or clinician associated with the participant, automatically transmitting a notification to the participant, automatically assigning the participant to a clinician and/or automatically scheduling a session, automatically notifying emergency services that the participant is in danger, etc.).

In a second set of variations, additional or alternative to the first, the technology confers the benefit of detecting that a participant should be escalated to immediate care in an emergency situation, such as in the case of suicidal ideation. In specific examples, the system and/or method can refer (e.g., automatically refer) the participant to immediate contact with a care provider (e.g., coach, clinician, emergency services/emergency responders, etc.), notify (e.g., automatically notify) the participant of resources which he or she can take part in and/or recommended next steps, and/or any other actions.

In a third set of variations, additional or alternative to those described above, the technology confers the benefit of automatically initiating one or more actions in response to detecting a recommended escalation. In specific examples, for instance, this can include automatically initiating any or all of: a communication (e.g., message) with a participant, care provider, and/or other individual (e.g., emergency contact of the participant, etc.); an assignment of a participant to another care provider; and/or any other action(s).

Figure 10:
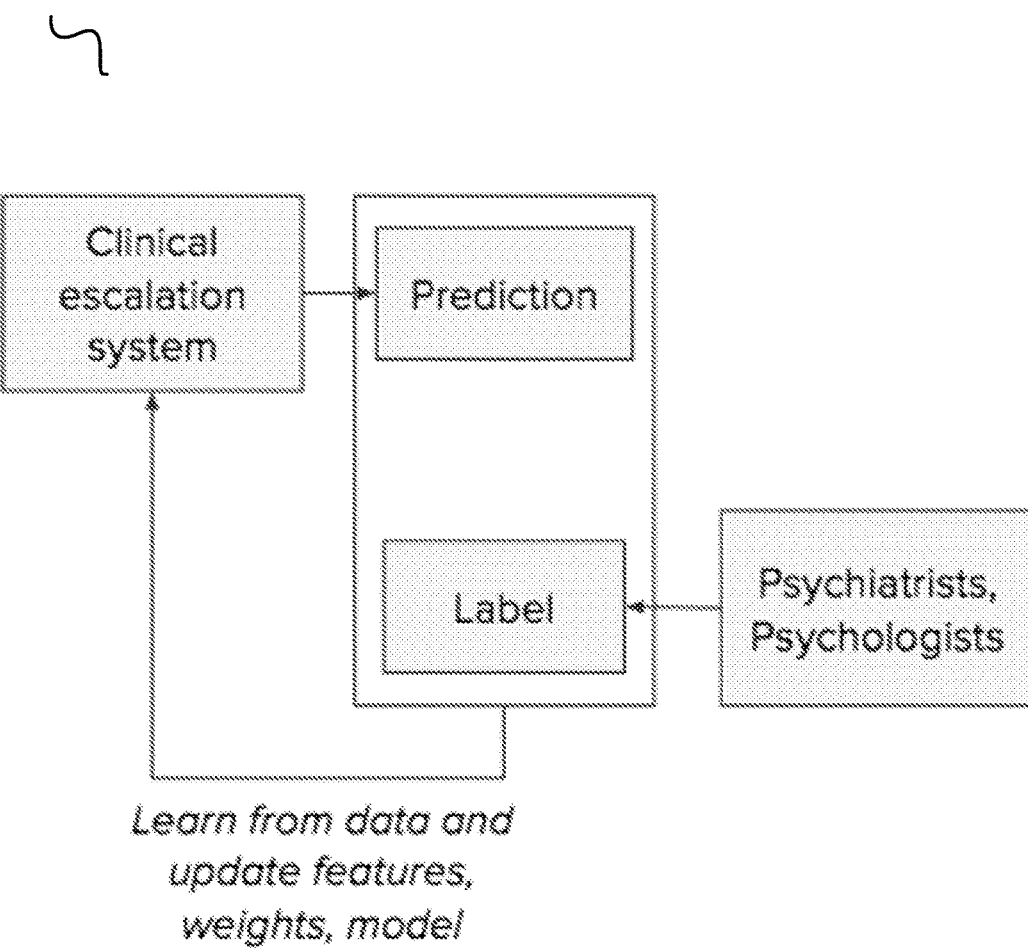
FIG. 10 is a schematic representation of a training of a model for computer-aided escalation.

In a fourth set of variations, additional or alternative to those described above, the technology confers the benefit of enabling consistent, repeatable, and robust detections of participants who need and/or could potentially benefit from a change in care level (e.g., escalations, de-escalations, etc.). In specific examples, this is enabled through a set of models trained with any or all of: clinical inputs (e.g., as shown in FIG. 10) and/or any other inputs from individuals experienced in the management of care for individuals; historical and/or aggregated information from a corpus of participants; and/or any other information. The technology can further function to enable the updating (e.g., retraining, refinement of parameters such as weights, etc.) of any or all models, such as based on learnings from participants in the program (e.g., success of participants who have been escalated).

In a fifth set of variations, additional or alternative to those described above, the technology confers the benefit of appropriately distributing responsibilities and/or workloads among multiple different care providers (equivalently referred to herein as care team members) and/or types of care providers in a digital health platform. In specific examples, a first set of care providers (e.g., coaches) is in contact with a majority of and/or all of the participants, wherein participants are selectively escalated to and/or engaged with a second set of providers (e.g., clinically-trained providers) in response to determining that the need of the participant exceeds the capabilities, qualifications, and/or responsibilities of the first set of providers.

In a sixth set of variations, additional or alternative to those described above, the technology confers the benefit of enhancing scalability of a digital health platform. In specific examples, for instance, the automatic detection of the need for clinical escalation can remove this as a responsibility of human care providers (e.g., coaches), thereby allowing them to take on a higher number of participants. Additionally or alternatively, the automatic detection can function to reduce a time for detecting that a participant should have a change in care, which can subsequently improve participant outcomes, prevent the increase and/or exacerbation of negative outcomes (e.g., increased thoughts of suicidal ideation, worsening depression, etc.).

In a seventh set of variations, additional or alternative to those described above, the technology confers the benefit of increasing a personalization and/or customization associated with responding to a detection that a participant should have an adjustment made to his or her care. In specific examples, for instance, information associated with the particular participant (e.g., his or her particular messages, historical information and/or progression of the participant, demographic information, etc.) is used to detect whether or not (and optionally specifically how) that particular participant should have his or her care adjusted (e.g., based on how he or she has been progressing or declining over time, based on previous escalations and/or de-escalations made for the participant, etc.).

In an eighth set of variations, additional or alternative to those described above, the technology confers the benefit of preventing repeat (e.g., redundant) triggering of the adjustment of a participant's care, such as through the detection and/or processing historical information associated with the patient and/or other users (e.g., a coach assigned to the participant) in the platform (e.g., detection that coach is already in the process of initiating an escalation of the participant, detecting that participant was escalated within a predetermined previous time threshold, etc.). This can additionally function to prevent notification fatigue for coaches, clinicians, and/or other users through the prevention of notifications to these users if they have already initiated and/or are in the progress of initiating a care plan adjustment.

In a ninth set of variations, additional or alternative to those described above, the technology confers the benefit of providing a traceability of, reasoning for, and/or specific evidence supporting a determination that the participant should have an adjustment made to his or her care plan. This can in turn function, for instance, to guide a user and/or increase an efficiency of a user (e.g., by pointing him or her to specific messages and/or other information which contributed to the determination) in initiating a proper action in response to the determination. In specific examples, for instance, at least a portion of the method is performed in accordance with a rule-based model (e.g., heuristics-based natural language processing [NLP] model), which enables the particular messages and/or other inputs which contributed to a determination to be easily identified and conveyed to a user. In additional or alternative specific examples in which the method employs a trained model and/or trained model architecture, the method can still employ a rule-based model and/or rule-based component (e.g., heuristics-based NLP model) which interfaces with the trained model and thereby still confers this traceability and transparency.

Additionally or alternatively, the system and method can confer any other benefits.

3. System 100

As shown in FIG. 1, a system 100 for computer-aided escalation can include and/or interface with any or all of: a set of user interfaces (equivalently referred to herein as dashboard or hubs), a computing system, and a set of models. Additionally or alternatively, the system can include and/or interface with any other suitable components.

The system 100 is preferably implemented in accordance with a digital platform, wherein a set of services (e.g., coaching, therapy, content, mental and/or physical health management, etc.) and/or interactions (e.g., communications, feedback, advice, etc.)—which can individually and/or collectively be referred to herein as "care"—are provided (e.g., digitally, remotely, etc.) to participants engaged in the digital platform. In a preferred set of variations, the digital platform includes a digital health platform in which the care provided to a participant is at least partially related to a mental health (e.g., mental state, depression state, happiness, mental stability, particular mental condition(s), etc.) of the participant, a physical health of the participant (e.g., fitness level, physical rehabilitation, etc.), and/or any combination. Additionally or alternatively, the digital platform can be suitably configured in any other ways and/or for any number of objectives (e.g., career goals, personal goals, educational goals, relationship goals, financial goals, friendship goals, social goals, etc.). Further additionally or alternatively, any or all of the digital platform can include and/or interface with any number of non-digital components and/or implementations (e.g., in-person care, in-person therapy, physical materials and/or goods, etc.).

The system 100 preferably functions to detect if a participant is potentially in need of (e.g., predicted to benefit from) an adjustment in care (e.g., care escalation, care de-escalation, emergency care, etc.) in the digital platform. Care herein can refer to herein and/or include any or all of: care within a digital platform, care outside of a digital platform (e.g., emergency services), features and/or intensity (e.g., tiers, levels, etc.) associated with care and/or intervention for the participant, any other types of care, and/or any combination. Additionally or alternatively, the system 100 can function to implement (e.g., automatically implement, facilitate, etc.) any or all of the adjustment (e.g., escalation, de-escalation, initiation, stopping/halting, etc.) in care. Further additionally or alternatively, the system 100 can perform any other suitable functions.

The system preferably interfaces with a set of users, wherein the set of users can refer to any or all of: participants, care team members, any other individuals, and/or any combination of users. The care team (equivalently referred to herein as care providers) preferably includes the individuals and/or entities (e.g., humans, bots, etc.) involved in the care (e.g., coaching, non-clinical care, clinical care, provision of tools and/or information, etc.) of the participant within the digital health platform and can include any or all of: coaches (e.g., who interact with the participants at all levels of care, who interact with participants at at least the lowest levels of care, etc.), supervisors (e.g., who supervise coaches, who supervise clinicians, etc.), clinicians (e.g., therapists, psychiatrists, psychologists, physicians, specialists, clinically-trained coaches, etc.), member support persons (e.g., users involved in supporting the care team members and/or participants, technical support persons, etc.), and/or any other individuals and/or entities. The set of participants (equivalently referred to herein as members and patients) preferably refers to individuals partaking in the digital platform (referred to herein as "receiving care") (e.g., receiving coaching, receiving clinical support, etc.), but can additionally or alternatively refer to any other suitable individuals.

The system can include and/or interface with a set of user interfaces (equivalently referred to herein as dashboards and/or hubs), wherein the set of user interfaces function to enable any or all users (e.g., in the digital health platform) to provide and/or receive information (e.g., from other users, from a computing system, etc.). As such, the user interfaces can include and/or provide any or all of: messaging platforms (e.g., with which users can exchange information), content (e.g., provided to a participant by his or her coach, provided to a participant automatically, etc.), notes sections (e.g., for a coach to record and/or share his or her observations of a participant, for a coach to communicate his or her observations to another coach and/or a supervisor and/or a clinician, etc.), and/or any other features and/or functionalities.

In some variations, each of the users is associated with a hub which provides and/or organizes the information accessible by each particular user, wherein the types of hubs can include any or all of: a coaching hub for coaches, a supervisor hub for supervisors, a member hub for members (equivalently referred to herein as participants), a clinical hub for clinicians, and/or any other suitable hubs. The hubs can be any or all of: the same (e.g., including the same features, including the same sections, etc.), different, and/or any combination. Additionally or alternatively, the hubs can be otherwise configured.

In preferred examples, any or all of the user interfaces can be implemented as and/or provided within one or more client applications executable on a user device (e.g., mobile user device, smartphone, laptop, tablet, etc.), wherein users can log into and/or otherwise access their respective interfaces (e.g., at various devices, at a mobile device, at a desktop device, etc.) through the client application. Each of the user interfaces is preferably in communication with and/or part of a computing system, preferably a remote computing system, wherein information associated with the interface is updated and/or shared through the remote computing system. Additionally or alternatively, information can be alternatively shared and/or updated (e.g., at local devices).

The care team preferably includes a set of coaches, wherein each of the set of coaches interacts with a set of members (equivalently referred to herein as participants), and optionally any or all of his or her: supervisors, member support persons, clinicians (e.g., assigned to the coach, assigned to the member, etc.), and/or any other suitable individuals and/or entities.

Each participant is preferably assigned a set of one or more coaches (e.g., wherein a primary coach is assigned to the member and responsible for communicating with the member while the primary coach is online and a set of backup coaches which can fill in for the primary coach if needed). Additionally or alternatively, the member can be assigned a single coach, a random coach (e.g., depending on when the member and the coach are online), and/or any other suitable coaches. The coach care team is preferably fixed but able to be updated for each member (e.g., in an event that a coach leaves or is matched with a different member, in an event that the member and a coach are not a good fit, etc.), but can additionally or alternatively be randomly determined and/or reassigned (e.g., upon login of the member and based on coaches online), dynamically determined, and/or otherwise determined or assigned.

The care team further preferably includes one or more clinical care team members (e.g., licensed clinicians, therapists, psychiatrists, physicians, specialists, trained coaches, etc.), equivalently referred to herein as clinicians, which can be assigned to (e.g., individually, through a clinician care team, etc.) a particular member or set of members, such as in response to an escalation. The clinicians are preferably able to communicate with members and any or all of the other members of the participant's care team (e.g., coaches, supervisors, other clinicians, etc.), but can additionally or alternatively be otherwise in communication (or not in communication) with one or more users.

The care team can optionally include one or more supervisors, wherein the supervisors preferably function to supervise (e.g., monitor, assess, perform quality assurance of, mentor, etc.) the coaches. Additionally or alternatively, the supervisors can function to approve and/or otherwise be involved in an escalation of a participant, supervise other care team members (e.g., clinical members), perform other roles (e.g., coaching), and/or perform any other suitable functions.

The care team can optionally include one or more member support persons, which function to assist any or all of the users in use of their hubs, such as in technical support. Additionally or alternatively, the member support persons can perform any other suitable tasks.

The system 100 preferably includes and/or interfaces with an adjustment detection subsystem including set of models and/or algorithms (e.g., artificial intelligence [AI] models and/or algorithms), wherein the set of models and/or algorithms functions to detect (e.g., determine, predict, etc.) that a participant's current level of care in the digital platform should be adjusted (e.g., increased in features, decreased in features, adjusted in features, etc.). This can include, for instance: detect that a participant should be escalated to a higher level of care, such as to another care team member (e.g., clinician, different coach, etc.), another program, emergency care, and/or any other outcomes; detect that a participant can and/or should receive a lower level of care (e.g., detecting that a participant has personally advanced and/or improved to a sufficient degree, detecting that the current level of care will not further benefit the participant, etc.); detect that a participant should receive different care (e.g., with different care team members, with care team members optimized for particular features associated with the participant, with different features and/or content and/or modules, etc.); and/or make any other detections. Additionally or alternatively, the set of models and/or algorithms can produce any other outcomes and/or be otherwise implemented.

The set of models preferably includes a set of rule-based models and/or algorithms, which can function to provide reliable, traceable, and explainable analyses of the participants. For instance, in some implementations of the system and method, data collected from participants (e.g., participant messages) are processed with a set of rule-based models and/or algorithms such that the particular pieces of data which contribute to a model/algorithm output (e.g., indication that the patient should be escalated to clinical care) can be easily identified (e.g., for review and/or verification, for further analysis by a care team member, etc.). This can also prevent limitations resulting from "black box" (e.g., end-to-end deep learning) data analysis approaches, such as: unexpected results (e.g., which could cause harm to the participant in an event that escalation is not detected when it should have been, which could cause unnecessary hassle to the participant in an event that escalation is recommended when not needed, etc.), a lack of explainability, and/or any other limitations. Additionally or alternatively, the set of rule-based models and/or algorithms can perform any other functions.

The set of rule-based models and/or algorithms preferably includes heuristics-based models and/or algorithms, and further preferably those which implement natural language processing (NLP) to analyze data according at least in part to a set of linguistics rules. Additionally or alternatively, the set of rule-based models and/or algorithms can include any other suitable models and/or algorithms.

Additionally or alternatively, the set of models and/or algorithms can include one or more trained (e.g., through supervised learning, through unsupervised learning, through semi-supervised learning, through reinforcement learning, etc.) models and/or algorithms, such as a set of machine learning models (e.g., deep learning models, neural networks, etc.). Additionally or alternatively, the set of models can include any all of: other models and/or algorithms, logic (e.g., hard-coded logic, programmed rules, etc.), decision trees, lookup tables, and/or any other tools.

The system 100 further preferably includes and/or interfaces with a computing system (e.g., as described above), wherein the computing system is configured to perform any or all of the processes of the method 200. Additionally or alternatively, the computing system can perform any other functions, such as storing the set of models, storing any or all of the set of inputs, and/or performing any other functions.

The computing system preferably includes a remote computing subsystem (e.g., cloud-based computing system) in communication with client applications executing the hubs. Additionally or alternatively, the computing system can include local computing subsystems (e.g., at user devices executing the client application), or any combination.

Additionally or alternatively, the system 100 can include any other suitable components and/or combination of components.

4. Method

As shown in FIG. 2, a method 200 for computer-aided escalation includes receiving a set of inputs S100 and processing the set of inputs to determine a set of outputs S200. Additionally or alternatively, the method 200 can include triggering an action based on the set of outputs S300 and/or any other processes. The method 200 can be performed with a system as described above and/or any other suitable system.

The method 200 functions to provide optimal care to participants, which can include, for instance, ensuring that participants are receiving care from (e.g., in contact with) the appropriate members of a care team and to escalate participants to higher levels of care in an event that a need for escalation is detected. In preferred variations, for instance, the method 200 can function to determine that a participant should be in communication with a trained clinician for a predicted acute mental health condition (e.g., clinical depression, suicidal ideation, etc.) and/or particular area of psychoanalysis, rather than remain only in contact with coaches (e.g., who are not qualified to provide guidance on, who are not qualified to exclusively provide guidance on, etc.). In additional or alternative specific examples, the method 200 can function to identify scenarios which should be treated as an emergency, such as detected suicidal ideation associated with a participant. In yet other additional or alternative specific examples, the method 200 can function to determine that a participant is ready to be de-escalated in care (e.g., moved to a lower level of care, moved to non-clinical care, reverted to a previous level of care, etc.), that participant would benefit to a different set of features and/or care team members, and/or the method 200 can otherwise assess how a participant is doing and whether or not an adjustment in their care could be beneficial.

Additionally or alternatively, the method 200 can function to continuously monitor participants for escalation or other adjustment(s) with little to no human effort, such as automatically with a set of models.

Further additionally or alternatively, the method 200 can perform any other functions.

The method 200 is preferably performed with a system 100 as described above, but can additionally or alternatively be performed with any other suitable system(s).

4.1 Method—Receiving a Set of Inputs S100

The method 200 includes receiving a set of inputs S100, which functions to receive information with which to perform the remaining processes of the method 200. Additionally or alternatively, S100 can function to trigger remaining processes of the method (e.g., in response to receiving each new message from a participant) and/or can perform any other suitable functions.

S100 is preferably performed initially in the method 200, but can additionally or alternatively be performed multiple times during the method 200 (e.g., continuously, at a predetermined frequency, in response to a trigger, etc.), in response to any other processes of the method 200, as part of and/or in parallel with any other processes of the method 200, continuously during user interaction with a digital platform (e.g., each time a participant provides a message, each time a care team member provides information at his or her interface, etc.), and/or at any other times.

The set of inputs are preferably received at a computing system (e.g., remote computing system) or set of computing systems (e.g., multiple computers), such as from one or more user interfaces (e.g., via a client application), but can additionally or alternatively be received from any other suitable sources.

The set of inputs preferably includes conversation information (equivalently referred to herein as communication information) from (e.g., between) one or more users, such as messages from a participant to one or more care team members (e.g., messages exchanged between a participant and a care team member). In preferred variations, for instance, the messages include those transmitted from a participant to a coach, but can additionally or alternatively include messages to any other care team member, messages from a care team member (e.g., to a participant, to other care team members, etc.). Additionally or alternatively, conversation information can be collected from any other users, such as, but not limited to, any or all of: a first coach and a second coach, a coach and a clinician, a coach and a supervisor, a clinician and a supervisor, a coach and a member support person, a supervisor and a member support person, a clinician and a member support person, a set of multiple participants (e.g., in a support group), and/or between any other users and/or entities.

The conversation information preferably includes a set of messages (e.g., typed messages, written messages, chats, audio messages, video messages, etc.), such as a set of messages exchanged with a messaging platform (equivalently referred to herein as a chat platform) of the set of user interfaces (e.g., hubs). Additionally or alternatively, the set of messages can be exchanged at a third-party client application (e.g., native messaging application on a user device, text messaging application, etc.) and/or through any other platform.

Additionally or alternatively, the conversation information can include any or all of: audio information (e.g., from a call), video information (e.g., from a video call and/or video conference), transcribed information (e.g., from a call and/or video), information derived from a conversation (e.g., perceived tone of a user in audio, perceived mood of a user in video, etc.), and/or any other conversation information.

The conversation information can optionally be received in association with any or all of: a predetermined time period (e.g., last week, last month, up to the last 6 weeks, last year, between the last week and the last month, any time periods bounded by these limits, etc.), a predetermined number of interactions (e.g., last 10 interactions of the participant with his or her coach, between the last interaction and the last 100 interactions, etc.), features of the conversation (e.g., a message length exceeding a predetermined threshold), and/or any other features. Additionally or alternatively, conversation information can be otherwise received.

In preferred first set of variations, S100 includes receiving a set of messages (e.g., single message, multiple set of messages, batch of messages, etc.) exchanged between a participant and his or her coach(es) or other care team members. Additionally, S100 can include receiving messages between the participant and any other care team members he or she interacts with, receiving other conversation information (e.g., audio calls between the participant and a coach, video calls between the participant and a clinician, etc.), and/or any other information.

In a second set of variations, additional or alternative to the first, S100 can include receiving a set of messages between a coach and a supervisor, such as a set of notes describing the coach's interactions with the participant.

In a third set of variations, additional or alternative to those described above, S100 can include receiving conversational information between a coach and a clinician and/or between a supervisor and a clinician.

The set of inputs can additionally or alternatively include participant information, such as any or all of: demographic information (e.g., age, sex, ethnicity, etc.), lifestyle information, historical information, medical information (e.g., medical history, clinical status indicating whether or not the participant is currently under the care of a psychologist and/or psychiatrist and/or therapist, history indicating whether or not the participant has previously been under the care of a psychologist and/or psychiatrist and/or therapist, etc.), preferences (e.g., communication preferences), and/or any other information. In specific examples, for instance, the set of inputs includes a clinical status of the participant, which indicates: whether or not the participant is engaged in clinical services within the digital health platform, whether or not the participant is engaged in clinical services (e.g., therapy, psychiatry, etc.) outside of the digital health platform (e.g., based on medical records, based on participant input, based on clinician input, etc.), and/or whether or not the participant is open to engaging in clinical services.

In a set of specific examples, the clinical status can be used to determine whether or not an action should be triggered in S300.

In another set of specific examples, the clinical status can be used to determine whether or not any or all of the remaining processes of the method 200 should be performed.

The set of inputs can additionally or alternatively include other inputs associated with the participants, such as, but not limited to: surveys, questionnaires, assessments (e.g., risk assessments of the participant initiated by a coach and/or other care team member), information from clinical sessions involving the participant (e.g., record that the participant has participated in a clinical session with a psychologist and/or psychiatrist and/or therapist, transcription of the session, video and/or audio data from the session, etc.), and/or any other input types.

In some variations, for instance, a coach or other care team member can request that the participant fill out a survey (e.g., upon suspicion by the care team member that the participant's mental health has changed), where the request can function to: prompt the performance of S200, adjust the frequency at which the participant data is analyzed in S200, and/or can perform any other functions. Additionally or alternatively, any or all of these inputs can be received according to a schedule (e.g., predetermined frequency), function to inform and/or prevent an action from being triggered in S300, and/or can perform any other function(s).

In a specific set of examples, mental health surveys (e.g., clinical surveys, depression surveys, Patient Health Questionnaire-9 [PHQ-9] surveys, Generalized Anxiety Disorder-7 [GAD-7] surveys, etc.) are administered (e.g., automatically through a participant dashboard) at a predetermined frequency (e.g., between every week and every 6 months, less frequently than every 6 months, etc.), where this predetermined frequency can optionally be adjusted (e.g., increased if the participant previously screened positive for depression in the past, adjusted during S300 and/or based on an output of S200, etc.).

The set of inputs can additionally or alternatively include flagged and/or otherwise selected information, such as message information flagged by a coach or other care team member. In specific examples, for instance, a coach can flag (e.g., annotate, mark, select, highlight, etc.) messages and/or message portions from a participant which may be concerning to the coach and/or desired to be further reviewed (e.g., by a supervisor, by a clinician, by one or models, etc.).

The set of inputs can additionally or alternatively include sensor data (e.g., from a set of sensors onboard a user device and/or mobile user device, and/or data collected from a set of supplementary devices (e.g., user device, mobile user device, biometric/biosignal detection device, set of sensors, etc.) associated with a participant, which can function, for instance, to provide information regarding any or all of: participant activities (e.g., how often the participant exercises, how often the participant leaves his or her home, how many hours the participant works per day, how social the participant is, etc.); participant communication (e.g., how often the participant communicates with individuals outside the platform); participant device usage (e.g., how much time the participant spends on his or her smartphone); biometric information (e.g., participant heart rate data); and/or any other information.

In some variations, for instance, the set of inputs includes any or all of the information as described in U.S. patent application Ser. No. 13/969,349, filed 16 Aug. 2013, now issued as U.S. Pat. No. 9,836,581; U.S. patent application Ser. No. 14/839,053, filed 28 Aug. 2015, now issued as U.S. patent Ser. No. 10/068,670; U.S. patent application Ser. No. 15/069,163, filed 14 Mar. 2016, now issued as U.S. patent Ser. No. 10/748,645; and U.S. patent application Ser. No. 17/463,432, filed 31 Aug. 2021, each of which is incorporated herein in its entirety by this reference.

Additionally or alternatively, the set of inputs can include any other information received from any users, predicted information (e.g., from one or more models), stored information (e.g., from one or more databases), 3$^{rd}$ party information (e.g., clickstream data associated with the participant, platform information such as login frequency of the participant, etc.), and/or any other information.

Additionally or alternatively, S100 can include any other suitable processes.

In a first set of variations, S100 includes receiving a set of inputs from a set of one or more user interfaces, where the set of one or more user interfaces includes at least a user interface associated with each of the set of participants in a digital platform, and wherein the set of inputs includes at least communication information from a set of messages associated with the participant. Additionally or alternatively, the set of inputs can include binary information regarding what other inputs and/or information has been received and/or triggered (e.g., a binary analysis of whether or not the participant is currently in the process of escalation and/or de-escalation, a binary indication of whether or not a risk assessment has already been performed for the participant, a binary indication of whether or not the participant is currently under the care of a psychiatrist and/or psychologist and/or therapist, etc.), information from (e.g., within) a set of surveys and/or assessments, sensor data from a device associated with the participant, and/or any other inputs.

4.2 Method—Processing the Set of Inputs to Produce a Set of Outputs S200

The method 200 includes processing the set of inputs to produce a set of outputs S200, which functions to assess the participant and determine whether or not a participant should be escalated and/or otherwise adjusted in care. Additionally or alternatively, S200 can function to inform the selection of an action to be performed in S300, prevent an action from being triggered in S300 (e.g., depending on the types of inputs received in S100), and/or can perform any other suitable functions.

S200 is preferably performed in response to S100 and based on any or all of the inputs received in S100, but can additionally or alternatively be performed multiple times during the method 200 (e.g., continuously, at a predetermined frequency, in response to a trigger, etc.), in response to any other processes of the method 200, as part of and/or in parallel with any other processes of the method 200, prior to any other processes of the method 200, and/or at any other times.

S200 is preferably performed automatically with an adjustment detection subsystem including a set of models and/or algorithms (e.g., as described above), but can additionally or alternatively be performed with a set of manual processes, and/or any combination.

In a preferred set of variations, each message received from a participant triggers a performance of S200, wherein S200 is performed on each message received from a participant. Additionally or alternatively, any or all instances of S200 can be triggered according to a predetermined frequency (e.g., once per week, once per month, between once per hour and once every month, less than once per month, greater than once per month, at any ranges bounded by these values, etc.), once a predetermined batch of messages has been received from a participant, according to a care level of the participant, according to the results of a previous iteration of the method 200, and/or at any other times.

In additional or alternative variations, any other inputs and/or a combination of inputs can function to trigger a performance of S200 and/or any or all of the remaining processes of the method, such as, but not limited to: the detection that a coach has initiated an assessment of the participant and/or any other flag from a coach or other care team member; a detection that the participant has asked for help and/or indicated that they are experiencing a particular condition (e.g., depression, suicidal ideation, etc.); a detection that the user has completed a survey; and/or the method 200 can be otherwise suitably triggered.

Additionally or alternatively, any or all of the set of inputs can be pre-processed to determine if S200 and/or any or all of the remaining processes of the method 200 should be performed (e.g., to preserve computational resources, prevent the method from being implemented if not required, etc.). The pre-processing can include any or all of the processes described below in S200, separate processes, processing any or all of the inputs with a trained model (e.g., to get an early prediction score of whether or not the participant should have his or her care plan adjusted, etc.), and/or any combination of processes.

In a set of specific examples, if a particular subset of inputs is detected in S100 and/or an analysis is otherwise made which indicates that the participant has already had his or her care changed (e.g., participant has had care changed within a predetermined time threshold, participant has already been escalated, participant has already been de-escalated, participant is already at the highest level of care in the platform, etc.) and/or a change in care of the participant is already in progress, any or all of the method 200 can be adjusted (e.g., certain processes not performed to save computational resources, S200 not performed, S300 not performed to prevent notification fatigue of care team members, etc.).

Further additionally or alternatively, any or all of the method 200 can be triggered according to a predetermined frequency and/or otherwise suitably triggered.

S200 preferably includes determining a set of one or more scores, wherein the score(s) preferably reflect a likelihood (equivalently referred to herein as a prediction) that a participant should have his care adjusted (e.g., escalated to advanced care, escalated to emergency services, de-escalated to a lower level of care, etc.). Additionally or alternatively, S200 can determine any other information, such as, but not limited to: historical trends associated with a participant (e.g., aggregated scores over a period of time which indicates whether the participant has been increasingly recommended to adjust care), aggregated information for multiple participants (e.g., aggregated scores for use in training and/or refining models and/or algorithms), a recommended adjustment type (e.g., escalation to clinical care, de-escalation to non-clinical care, etc.), temporal parameters associated with the recommended adjustment (e.g., urgency level, recommended timeframe at which to perform the adjustment), a predicted mental condition and/or state associated with the participant, and/or any other information.

Any or all of the scores are preferably produced with a set of models, wherein the set of models preferably includes a set of rule-based models, but can additionally or alternatively include any or all of: a set of machine learning models (e.g., deep learning models, neural networks, convolutional neural networks, reinforcement learning models, etc.), algorithms, equations, decision trees, lookup tables, and/or any other tools.

The set of scores is preferably determined based on any or all of: inputs from one or more users (e.g., coaches, supervisors, etc.); inputs from one or more physicians (e.g., clinicians) treating the participant (e.g., therapists, psychiatrists, primary care physicians, etc.); features from a current communication of the participant (e.g., messaging/chats between the participant and a coach, transcript of a phone call between the participant and a coach, transcript of a video conference between the participant and a coach, etc.); experience information associated with any or all of: a set of symptoms experienced by the participant, a set of traumatic events experienced by the participant, a medical history of the participant (e.g., previous diagnoses, previous treatment, etc.), and/or any other experience information; any or all of the inputs received in S100; and/or any other suitable inputs.

In a preferred set of variations (e.g., as described below), determining the score(s) at least partially includes processing conversation information to detect a set of features (e.g., topics, words, etc.) associated with the conversation information, such as any or all of: particular symptoms associated with a mental health condition, indications of self-harm and/or potential self-harm, a diagnosis (e.g., current diagnosis of a participant, prior diagnosis of a participant, predicted diagnosis of a participant, clinical depression diagnosis, bipolar disorder diagnosis, suicidal ideation diagnosis, etc.), therapy history (e.g., participant's participation in therapy and/or psychiatry), medication history, emotion information (e.g., moodiness, emotional severity, etc.), communication clarity (e.g., communication style of the participant, openness of participant, etc.), and/or any other features.

In additional or alternative variations, processing conversation information includes automatically analyzing (e.g., with one or more models) chat transcripts between the participant and one or more care team members (e.g., coach). This preferably includes, for instance, analyzing the chat transcripts with one or models to check for a particular set of words and/or phrases. The particular set of words and/or phrases preferably includes a predetermined set of words (e.g., as selected by a set of clinicians and/or clinical literature, as selected through an optimization process, as learned by a machine learning model, etc.), but can additionally or alternatively include a dynamically determined set of words, and/or any combination. In specific examples, for instance, the set of words includes words associated with any or all of: a set of medications (e.g., depression medication), a set of mental health conditions (e.g., post-traumatic stress disorder, bipolar disorder, depression, anxiety, panic attack, etc.), a set of emotions, a set of life events (e.g., recent tragedy, stressful situations, etc.), and/or any other words.

The set of words can be specific to a particular mental health condition, specific to a particular user, and/or otherwise determined. Additionally or alternatively, the set of words can be uniform among all participants and/or otherwise determined.

In a preferred set of variations, S200 includes checking for a predetermined set of words in the chat transcripts between the participant and his or her coach(es).

Figure 7:
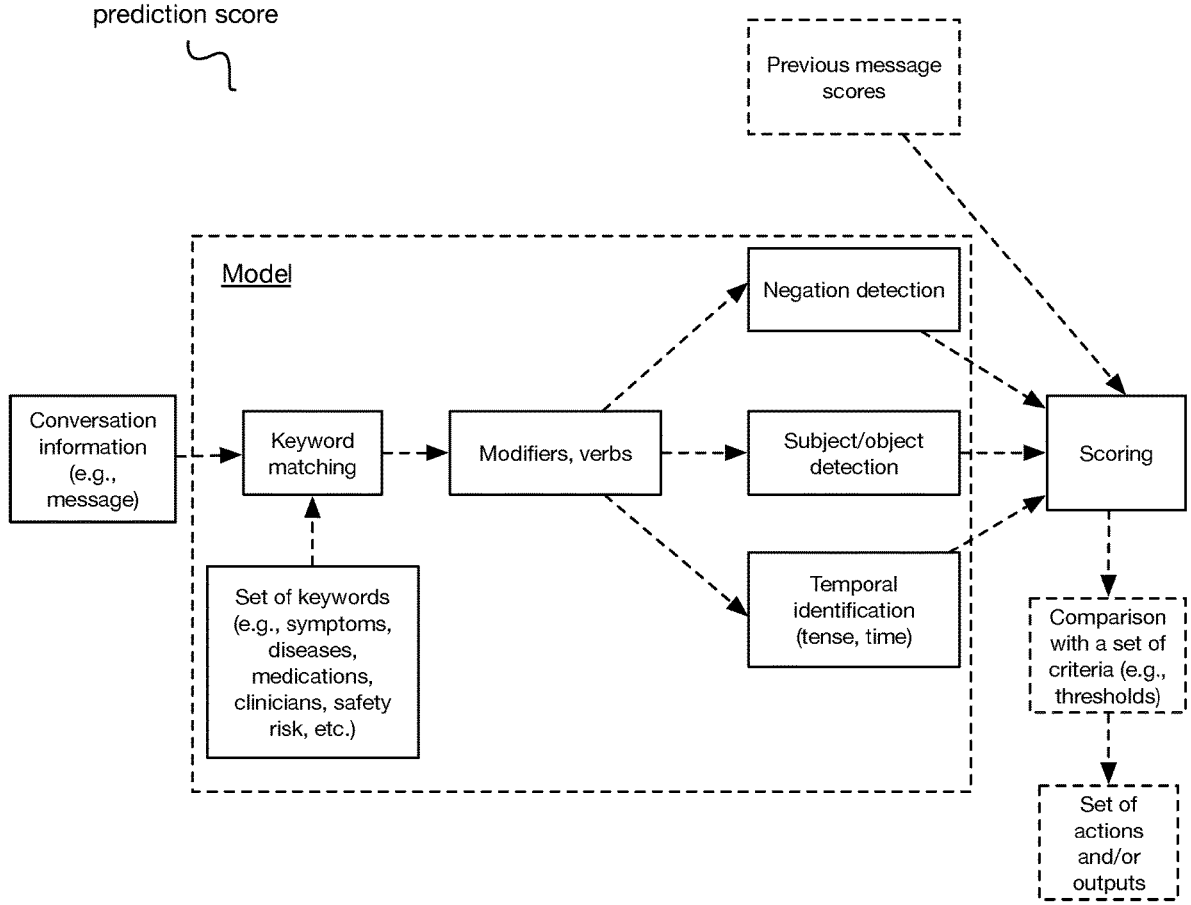
FIG. 7 is a schematic of an example of an adjustment detection subsystem for computer-aided care adjustment.

Analyzing the conversation information can additionally or alternatively include checking for features associated with the set of words, such as any or all of: an occurrence of the set of words (e.g., number of times a particular word is mentioned, number of times any word within a predetermined set is mentioned, etc.), a spatial relationship to other words (e.g., proximity to another word of the set within the same message, proximity to a modifier of the word, etc.), a temporal relationship to other words (e.g., time since the same word was last mentioned, time since another word in the set was mentioned, etc.), whether or not the word is self-referential (e.g., participant is experiencing a particular symptom vs. a friend of the participant experiencing the symptom), whether or not the word was mentioned recently, whether or not the word is negated (e.g., "not depressed" vs. "depressed"), and/or any other word and/or message features. In specific examples (e.g., as shown in FIG. 7), for instance, a set of keywords is checked for in the conversation information, wherein the keywords and any associated words (e.g., modifiers, verbs, etc.) are checked for with respect to negation detection (e.g., "I am not depressed"

rather than "I am depressed"), subject/object identification (e.g., "I am depressed" rather than "my sister is depressed"), temporal identification (e.g., "I had suicidal thoughts 10 years ago" vs. "I am having suicidal thoughts"), and/or any other features.

Figure 3:
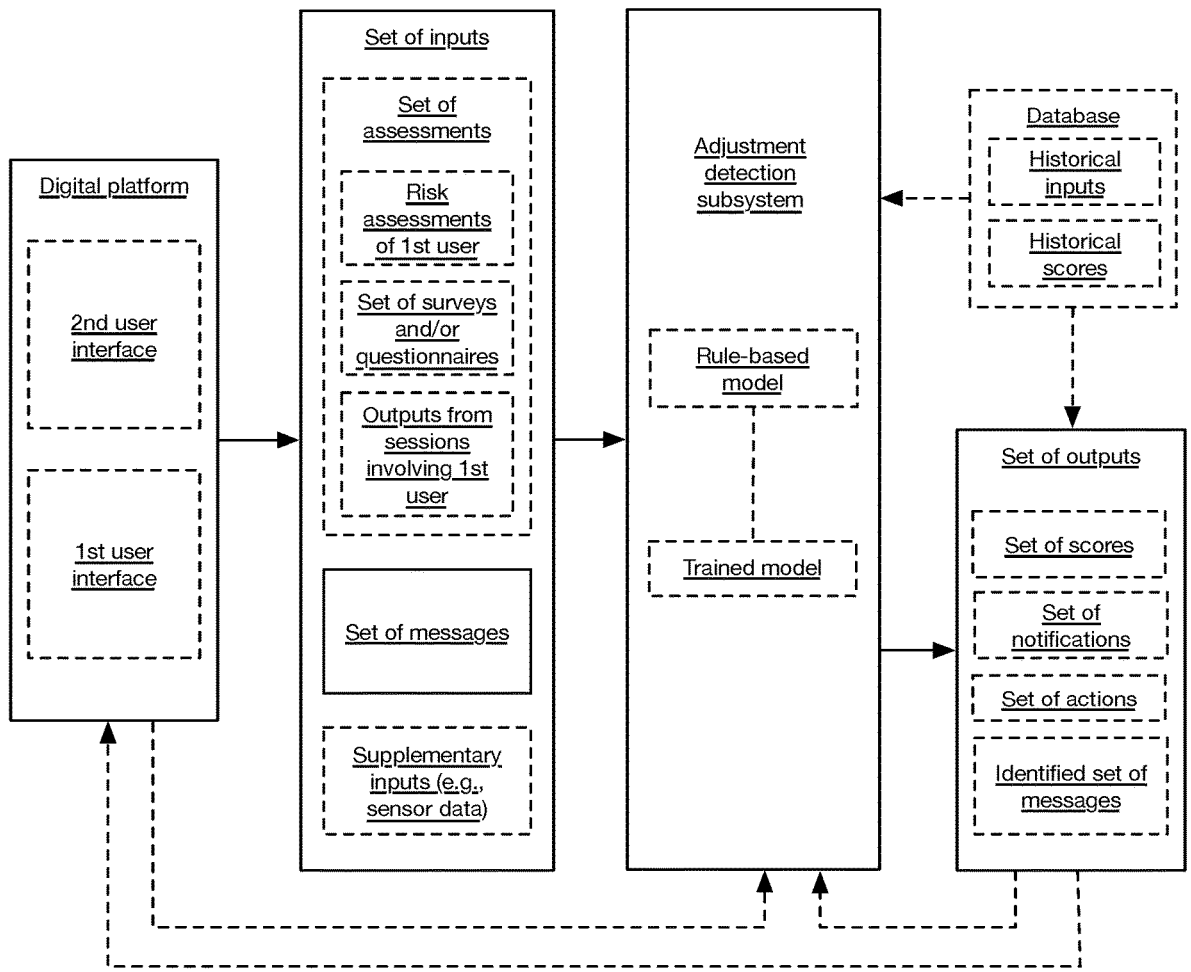
FIG. 3 is a schematic variation of a system and associated information exchange for computer-aided care adjustment in a digital health platform.

S200 is preferably performed (e.g., as shown in FIG. 3) with an adjustment detection subsystem which can include any or all of: one or more rule-based models and/or algorithms, one or more trained models and/or algorithms, and/or any combination of models and/or algorithms.

The adjustment detection subsystem preferably functions to determine whether or not a participant should be escalated to more advanced care (e.g., clinical care, emergency care, etc.). As such, the set of models and/or algorithms can function to detect information within the set of inputs which a coach or other user may not perceive or easily perceive. This can include, for instance, the development of a mental health condition which happens gradually (e.g., over time), subtly, unexpectedly, in absence of a participant's desire to make his or her mental health condition known to a coach, and/or mental health conditions which occur in any other way(s). Additionally or alternatively, any or all of the mental health conditions can be known to a coach and/or easily detectable by a coach (e.g., wherein the coach flags the relevant information).

The adjustment detection subsystem (e.g., set of models and/or algorithms) is preferably at least partially determined (e.g., trained, weighted, etc.) based on input from a set of clinicians (e.g., therapists, psychiatrists, psychologists, physicians, etc.), clinician-related material (e.g., journal publications, guidelines, materials describing best practices, clinician notes, etc.), and/or any other health-related information (e.g., mental health information, psychology information, physical health information, etc.). Additionally or alternatively, the set of models and/or algorithms can be determined (e.g., trained, updated and/or retrained, optimized, etc.) based on information from prior participants in the platform, non-clinical materials (e.g., coaching materials), and/or any other information.

Figure 6:
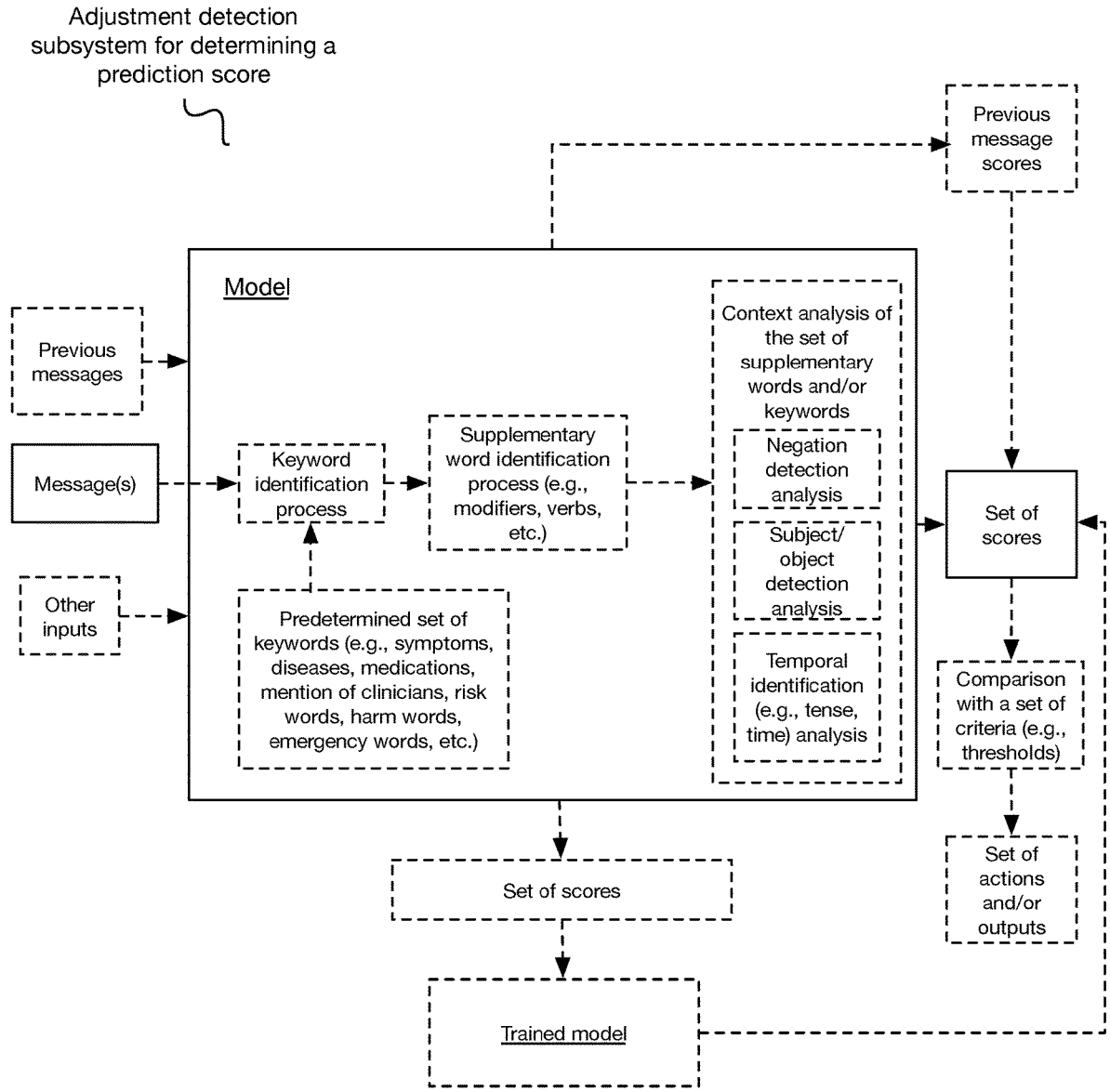
FIG. 6 is a schematic variation of an adjustment detection subsystem for computer-aided care adjustment.

The adjustment detection subsystem (e.g., as shown in FIG. 6) preferably includes a set of rule-based models and/or algorithms (e.g., heuristics-based NLP model), which processes the language in one or more inputs received in S100 to produce a set of scores. The set of inputs processed in the rule-based models preferably includes one or more messages received from the participant, but can additionally or include other communication information, the content of surveys and/or assessments, and/or any other inputs.

The set of rule-based models and/or algorithms can optionally include any number of sub-processes, such as any or all of: a keyword identification process, a supplementary word identification process, a context analysis process, and/or any other sub-process.

The set of rule-based models and/or algorithms preferably includes a keyword identification process, which functions to identify a set of keywords in the set of inputs (e.g., message), which can in turn function to identify whether or not the inputs are relevant for further processing, identify which subset of a set of outputs (e.g., particular mental health condition, escalation vs. de-escalation, etc.) are most likely and/or remaining as candidates for further consideration, and/or can perform any other functions.

The keyword identification process preferably checks for a set of particular keywords in any or all of the set of inputs, where the words are related to a particular set of mental health conditions and/or mental health risks associated with the participant. These can include, for instance, words associated with any or all of: symptoms (e.g., "depressed," "blue," "moody," "sad," "scared," "hope," etc.), diseases (e.g., "depression," "depressed," "delusions," "angry," etc.), medications, mention of clinicians and/or clinical care (e.g., mention of "psychologist," "psychiatrist," "therapist," "doctor," "counselor," "shrink," "therapy," "counseling," etc.), risk and/or harm and/or emergency words (e.g., "suicide," "cutting," "hurting," "abuse," "kill," "die," etc.).

The set of keywords preferably includes a set of predetermined words (e.g., predetermined list of words, adjusted list of words based on aggregated data from previous participants, etc.), but can additionally or alternatively include dynamically determined words, participant-specific words, and/or any other words.

The set of rule-based models and/or algorithms further preferably includes a supplementary word identification process, which functions to identify a set of supplementary words associated with the set of keywords (e.g., for further processing with a context analysis process). The set of supplementary words are preferably associated with a word type (e.g., part of speech, grammatical type, tense, etc.) and identified with respect to the set of keywords, such as based on a placement of the supplementary words in a sentence and/or relative to the keywords (e.g., immediately prior to the keyword, immediately after the keywords, within a predetermined number of words relative to the keyword, etc.), based on a set of linguistics rules, based on a diagramming of a sentence, and/or based on any other features. In a preferred set of variations, the set of supplementary words includes a set of modifiers and a set of verbs in the sentence. Additionally or alternatively, the set of supplementary words can include any or all of: adverbs, nouns, adjectives, descriptors, and/or any other words.

The set of rule-based models and/or algorithms further preferably includes a set of context analyses, which function to determine a set of scores (and/or a set of weights of sub-scores which are used to determine the set of scores) associated with the set of inputs (e.g., weight the outputs used in determining the scores). The set of context analyses further preferably function to determine a relevance of the set of keywords and/or set of supplementary words to a set of potential conditions associated with the participant. The set of context analyses can include multiple analyses (e.g., performed in parallel, performed in series, performed for each of the set of keywords, etc.), a single analysis, and/or any number of analyses. The set of context analyses are preferably performed at least in part based on the set of supplementary words and the set of keywords, but can additionally or alternatively be performed based on a subset of these, based on other sub-processes, and/or based on any other information.

The set of context analyses can optionally include a negation detection analysis, which functions to determine whether or not a keyword is positively recited. In preferred variations, for instance, the negation detection analysis analyzes the set of supplementary words to determine if they function to negate the keyword (e.g., "not" in "I do not have depression" or "I have not seen a therapist"; "no" in "I am taking no medications," or "I have no symptoms of depression," or "I have no experiences of suicidal ideation"; etc.) and/or a sentiment of the sentence (e.g., indicating that the user is actually not experiencing depression despite utilizing keywords which alone might suggest that they are). In an event, for instance, that it is determined that keywords associated with depression and/or suicidal ideations and/or mental health risks are negated, the contribution of these keywords to the score can be down-weighted (e.g., scaled down, scaled with a scaling factor less than 1, etc.) and/or negated and/or made to be zero, and/or any further processes can be terminated.

The set of context analyses can optionally additionally or alternatively include a subject/object detection analysis which functions to determine, in an event that a keyword is detected, whether or not the keyword (and/or associated supplementary words) applies to the participant (e.g., wherein keywords which do not apply to the participant are ignored, wherein the score is not impacted by such keywords, etc.). For instance, the subject/object detection analysis can function to differentiate "My mom has depression" from "I have depression," and thereby impact the score accordingly (e.g., wherein a participant with the latter message has a score which is more biased toward recommending that the participant be escalated to clinical care). This is preferably determined based on the set of supplementary words, but can additionally or alternatively be determined based on any other words, features, and/or information.

The set of context analyses can optionally additionally or alternatively include a temporal identification analysis, which functions to determine temporal parameters associated with the set of keywords (e.g., based on the set of supplementary words such as based on a tense of the supplementary words), such as: how recently the keyword was relevant to the participant (e.g., "I was suicidal 10 years ago" vs. "I am currently suicidal"; "I used to have depression" vs. "I have depression"; "I don't feel hopeful" vs. "I'm afraid I won't be hopeful in the future"; etc.). The temporal parameters can optionally be used to weight the score(s) (e.g., downweight if the associated time period is in the past, downweight if the associated time period is in the future, downweight if the associated time period deviates from present time by more than a predetermined threshold, downweight according to a scaling factor corresponding to the duration of time, etc.), and/or can be used in any other suitable ways.

Additionally or alternatively, any other analyses can be performed.

Further additionally or alternatively, any or all of the sub-processes of the adjustment detection subsystem can be performed with a set of trained models and/or algorithms.

Figure 8:
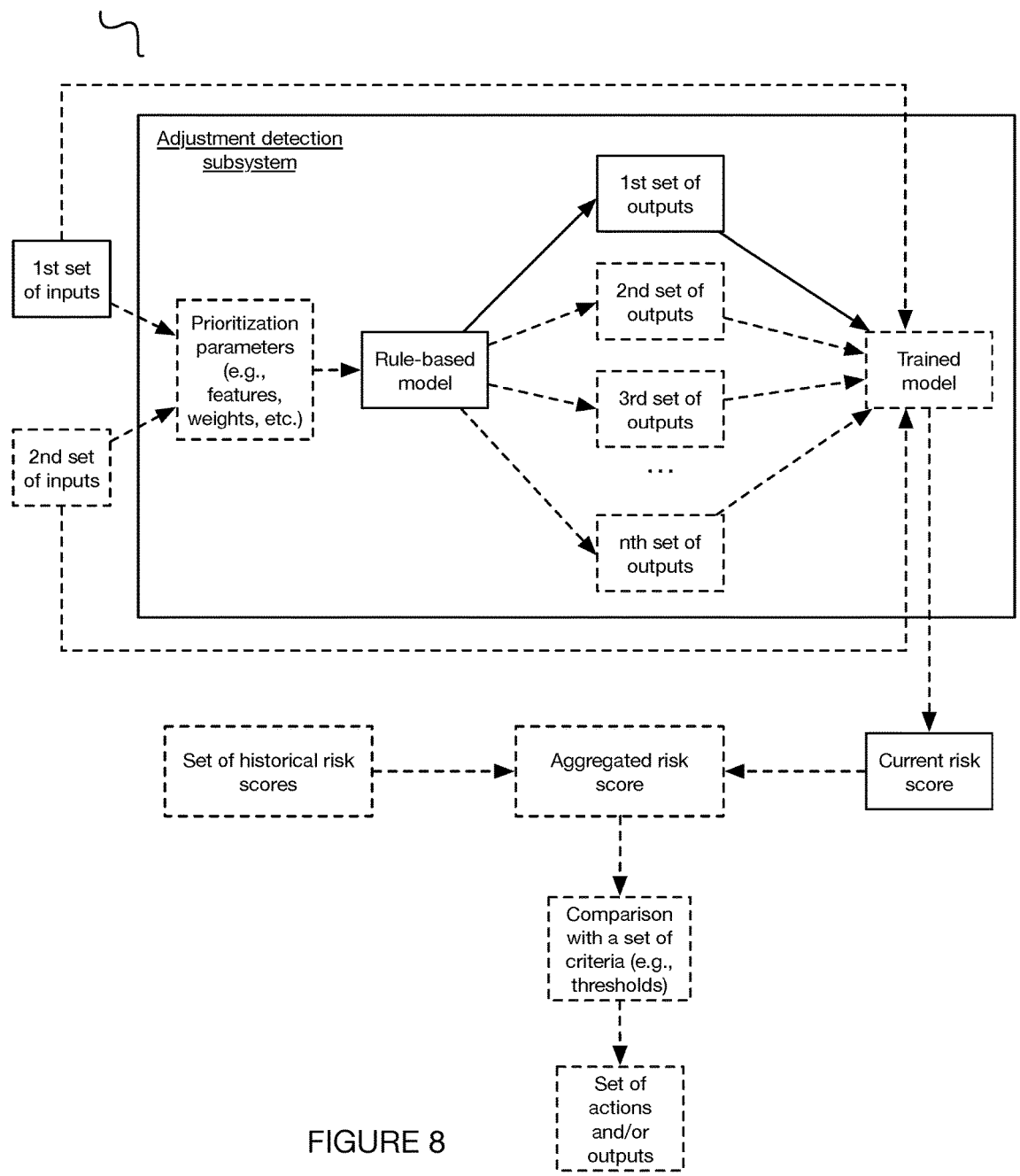
FIG. 8 is a schematic variation of an adjustment detection subsystem involving rule-based and/or trained models for computer-aided care adjustment.

Further additionally or alternatively, any or all of the rule-based models and/or algorithms can interface with a trained architecture, such as a set of trained models and/or algorithms (e.g., for prediction, for feature weighting, as shown in FIG. 8, etc.).

Figure 9:
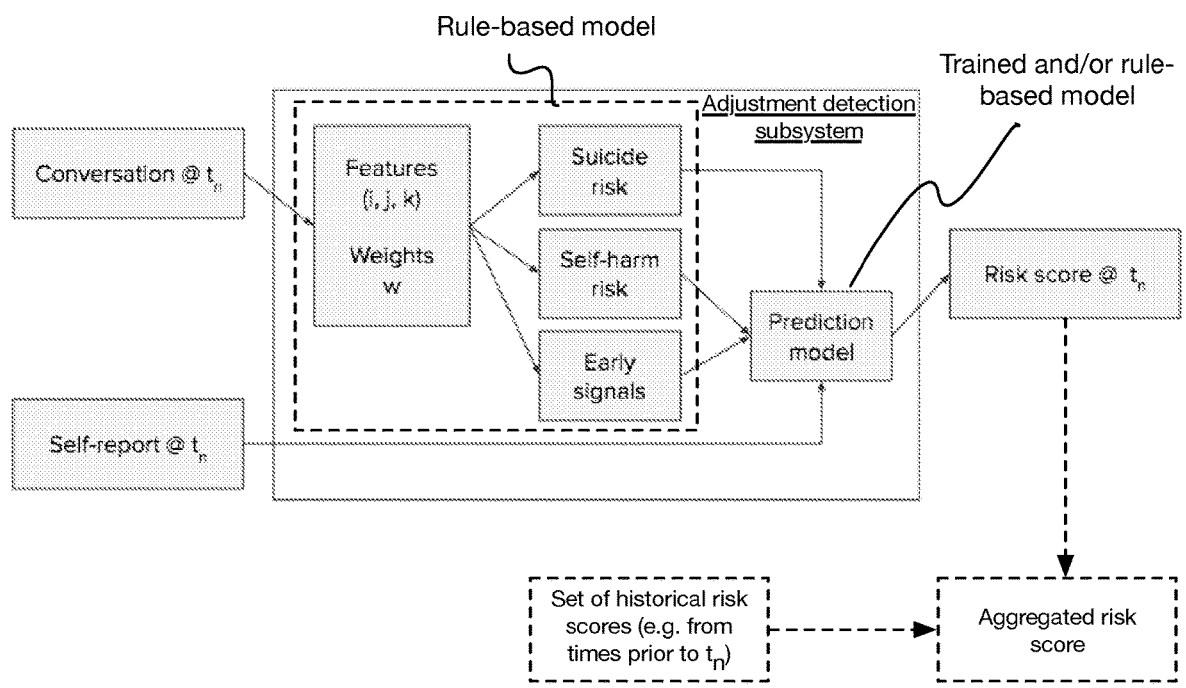
FIG. 9 is a schematic example of an adjustment detection subsystem involving rule-based and/or trained models for computer-aided care adjustment.

In a set of variations (e.g., as shown in FIG. 8, as shown in FIG. 9, etc.), for instance, a rule-based model is performed within the adjustment detection subsystem, wherein the set of inputs and/or the set of outputs produced by the rule-based models are weighted according to a set of learned prioritization parameters (e.g., features, weights, etc.).

In an additional or alternative set of variations, for instance, one or more of a set of machine learning models is trained (e.g., with supervised learning, with semi-supervised learning, etc.) based on labeled data collected from a set of clinicians. In specific examples, for instance, the labeled data includes portions of chat transcripts between a participant and a coach in which the participant provides information which should escalate him or her to clinical care. Additionally or alternatively, one or more machine learning models can be trained with unsupervised learning, one or more machine learning models can be trained based on other data, any or all of the set of models can be untrained (e.g., rule-based), and/or the set of models can be otherwise determined.

S200 can optionally include applying weights (e.g., as shown in FIG. 9) to any or all of the set of inputs (e.g., prior to processing by the adjustment detection subsystem, learned weights as described above, etc.). The set of weights can indicate, for instance, any or all of: a relevance of an input (e.g., to a particular condition and/or suspected condition, to other inputs, to historical inputs, to escalation generally, etc.); a confidence associated with an input; a severity associated with an input; an incidence of an input (e.g., relative to a total volume of inputs, relative to related inputs, etc.); and/or any other features. Additionally or alternatively, the inputs can be absent of weights and/or otherwise modified.

The set of scores produced with the adjustment detection subsystem can include any or all of: a binary score (e.g., indicating whether or not to escalate the participant), a non-binary score (e.g., indicating a value in a range), and/or any combination of scores. Additionally or alternatively, the set of outputs of the adjustment detection subsystem can include one or more qualitative outputs, such as any or all of: a recommendation for escalation, a recommendation for a particular type of escalation, an automated message (e.g., to send to a participant, to send to a coach, to send to a clinician, etc.), and/or any other outputs.

In a first set of specific examples, the set of outputs of the set of models and/or algorithms includes a score value along a range of values, wherein the score value indicates a prediction of any or all of: whether the participant should be escalated to a higher level of care (e.g., contact with a clinician), whether the participant should be de-escalated to a lower level of care, whether the participant should remain at his or her current level of care, and/or any other indications. Additionally or alternatively, the score value can reflect a confidence in a prediction that a participant should be escalated to a higher level of care, an urgency of escalating a participant to a higher level of care, and/or any other information.

In a second set of specific examples, the set of outputs of the set of models includes a binary score value, wherein the binary score value indicates either that the participant should be escalated to a higher level of care or that the participant should not be escalated to a higher level of care.

The set of outputs can be sent to any or all of: a supervisor (e.g., for the supervisor to review and then instruct the coach), a coach, a clinician, the participant, any combination of users, and/or any other individuals. Additionally or alternatively, the set of outputs can be used to trigger one or more actions in S300.

The set of scores can optionally be compared with one or more thresholds (e.g., time thresholds, occurrence thresholds, etc.), processed with one or more decision trees, processed with one or more models, and/or otherwise processed. In specific examples, a score is compared with one or more thresholds, such that, for instance, in an event that the score exceeds a threshold, the participant can be recommended to be escalated. Additionally or alternatively, in an event that the score is below a threshold, the participant can be recommended to be de-escalated. The set of thresholds are preferably predetermined, but can additionally or alternatively be dynamically determined (e.g., based on previous scores associated with the participant), and/or otherwise determined. Further additionally or alternatively, the set of scores can be analyzed with machine learning and/or with any other processes.

The set of scores can optionally include multiple scores which can be determined, compared with individual thresholds, and/or inherently prioritized according to a severity of a condition/scenario (e.g., based on a particular keyword and/or grouping of keywords) which the score quantifies. In some variations (e.g., as shown in FIG. 9), for instance, in an event in which a set of inputs are being analyzed to determine if a participant should be escalated to clinical care and/or emergency care, a set of multiple output scores (e.g., suicide risk score, self-harm risk score, early signals score, etc.) are produced (e.g., based on particular associated keywords) which are each associated with their own levels of severity (e.g., severity of suicide risk higher than self-harm risk, self-harm risk higher than early signals risk, etc.), where thresholds associated with each of these scores can be determined according to this severity (e.g., threshold required to be exceeded for suicide risk is lower than that for self-harm risk, etc.).

Any or all of the set of scores can optionally further be determined based on historical information associated with the participant, such as any or all of: a set of previously determined scores, prior inputs (e.g., previous messages, the last predetermined number of messages of the participant to a coach, messages from the last predetermined number of interactions between the participant and his or her coach(es), etc.), prior escalation recommendations and/or prior escalations, historical information associated with other participants (e.g., aggregated information from prior participants having similarities to the present participant).

Figure 4:
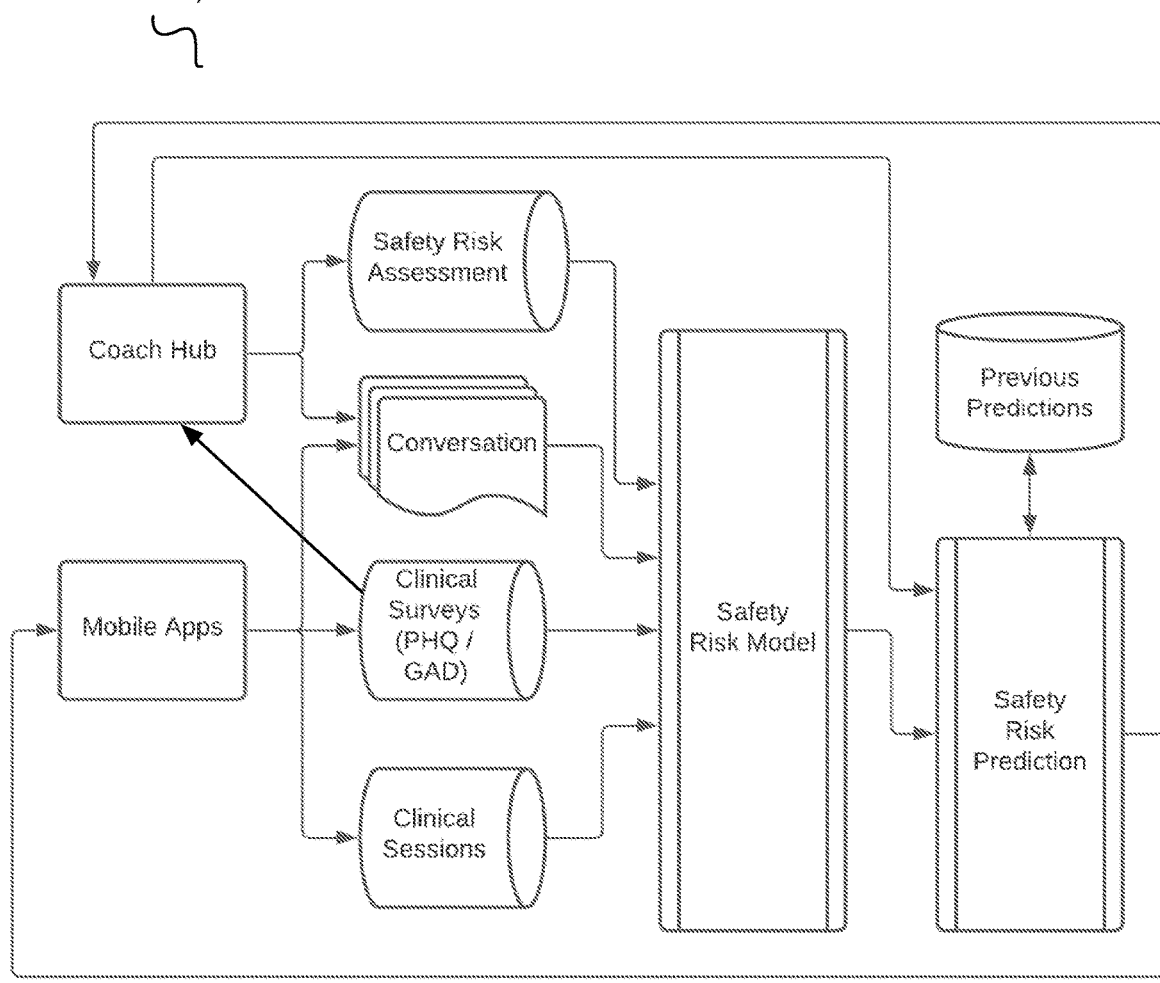
FIG. 4 is a schematic representation of a first variation of a workflow for computer-aided care adjustment.

In a first set of variations (e.g., as shown in FIG. 4), for instance, in determining whether or not a participant should be escalated to an emergency action (e.g., in an event of suicidal ideation), a prediction score associated with the participant (e.g., safety risk score) can be determined based on previous prediction scores (equivalently referred to herein as previous predictions) determined for the participant (e.g., with the same model(s)). In a specific set of examples, a safety risk prediction score is determined for each interaction (e.g., session, chat, set of messages exchanged proximally in time, etc.) of the participant with his or her coach (e.g., aggregated from all messages exchanged between the participant and his or her coach during the interaction), wherein the current prediction score takes into account the set of scores determined based on a predetermined number of these previous interactions (e.g., last 5 interactions, last 10 interactions, last 20 interactions, last 100 interactions, between the last 2 and last 50 interactions, etc.). In another set of specific examples, the safety risk prediction score can be determined based on all prior interactions (e.g., based on exceeding a running score associated with all interactions of the participant, based on aggregating prior scores with the current score, etc.). Additionally or alternatively, the safety risk prediction score can be determined in absence of historical information and/or can be otherwise determined.

Figure 5:
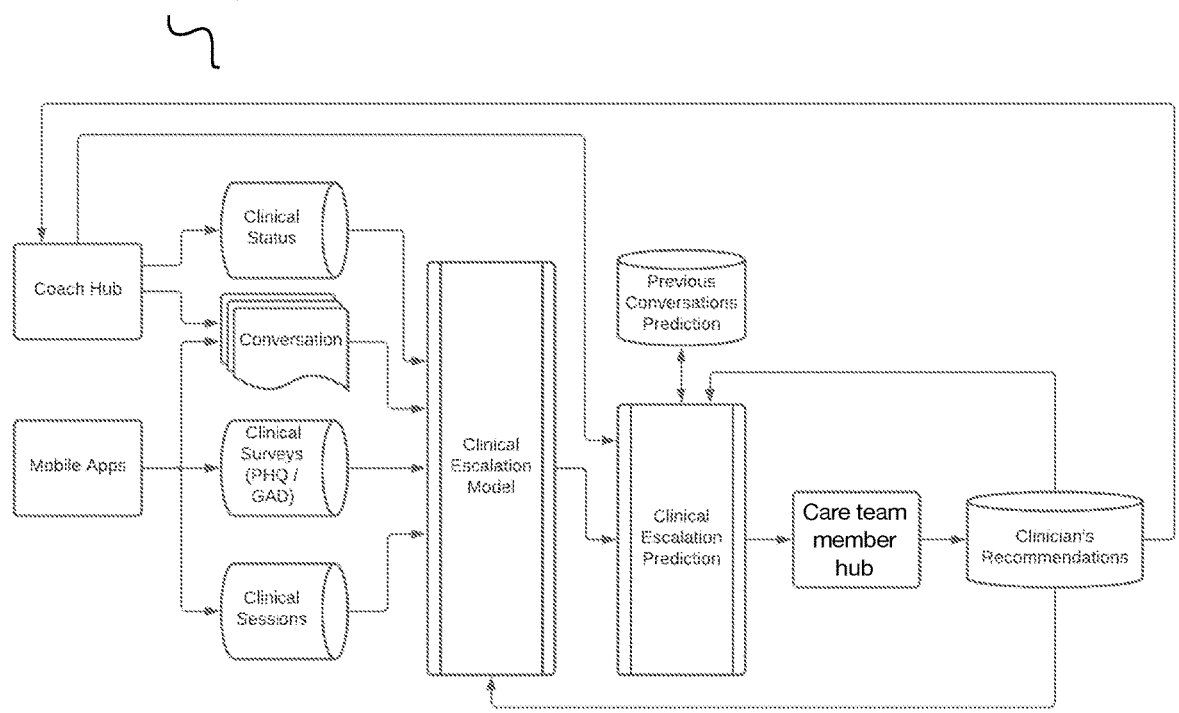
FIG. 5 is a schematic representation of a second variation of a workflow for computer-aided care adjustment.

In a second set of variations (e.g., as shown in FIG. 5), for instance, in determining whether or not a participant should be escalated to care involving a clinician, a prediction score associated with the participant is determined based on previous conversation prediction scores (equivalently referred to herein as previous conversation predictions) determined for the participant (e.g., with the same model(s)). In a specific set of examples, a clinical escalation score is determined at least in part based on conversations between the participant and his or her coach during a predetermined time period (e.g., all messages exchanged between the participant and his or her coach during the prior week, all messages exchanged between the participant and his or her coach during the prior month, all messages exchanged between the participant and his or her coach during the prior year, etc.). In another set of specific examples, the clinical escalation prediction score can be determined based on all prior conversations and/or any other historical information (e.g., non-conversational historical inputs). Additionally or alternatively, the clinical escalation prediction score can be determined in absence of historical information and/or can be otherwise determined.

In a third set of variations, each message from the participant is processed with a set of adjustment detection subsystems (e.g., one for clinical care adjustment, one for suicidal ideation detection, etc.) to determine a set of one or more scores. In response to determining the set of scores (and/or in parallel with determining the set of scores), a set of historical scores for the participant (e.g., scores associated with a predetermined last set of messages, running aggregated scores, scores from between the last message to the last 100 messages, scores from the last 2-10 messages, scores from the last 1-5 messages, etc.) can be retrieved and referenced to assess any or all of: whether the score and/or its implications (e.g., participant should be escalated) is a one-time event, new event, continuing risk, and/or any other assessments, which can optionally be surfaces to the coach or other care team members, used to determine an action in S3o, and/or be otherwise used.

Additionally or alternatively, S200 can include any other suitable processes.

In a first set of variants (e.g., as shown in FIG. 4, as shown in FIG. 6, as shown in FIG. 7, etc.), S200 includes assessing the set of inputs with a safety risk model (e.g., set of rule-based models, set of rule-based models and/or trained model(s), set of trained models, etc.) to determine whether or not a safety risk is associated with the participant. This is preferably performed with a set of rule-based models which determine a set of one or more scores (e.g., according to which keywords are detected), such as, but not limited to: a desperation score, a self-harm score, a suicidal ideation score, and/or any other scores. These scores can then be: compared with a set of multiple thresholds, aggregated and compared with a single threshold, and/or otherwise processed. Additionally, the set of scores can optionally be determined based on and/or compared with historical information associated with the participant, such as a set of historical scores. In a set of specific examples, for instance, in comparing any or all of the scores with a set of thresholds, the historical scores can be included (e.g., downweighted, scaled with a scaling factor less than 1, etc.) and aggregated with the current score(s)) in the score. In another set of specific examples, the historical scores are compared with the current scores to determine a trend (e.g., improving, not improving, etc.) associated with the participant. In yet another set of specific examples, historical inputs can be processed with current inputs in the adjustment detection subsystem.

In a set of examples, S200 is performed based on a set of one or more messages from the participant.

In additional or alternative examples, S200 is performed based on other inputs (e.g., sensor data, survey data, etc.).

In a second set of variants (e.g., as shown in FIG. 5, as shown in FIG. 6, as shown in FIG. 7, etc.), S200 includes assessing the set of inputs with a clinical escalation model (e.g., set of rule-based models, set of rule-based models and/or trained model(s), set of trained models, etc.) to determine whether or not the participant should be escalated to clinical care (e.g., have a clinician as part of his or her care team). This is preferably performed with a set of rule-based models which determine a set of one or more scores (e.g., according to which keywords are detected), such as, but not limited to: how likely it is that the participant is taking medication; how likely it is that the participant has experienced trauma; how likely it is that the participant is currently seeing a clinician (e.g., psychologist, psychiatrist, therapist, etc.); and/or any other scores. These scores can be then be: compared with a set of multiple thresholds, aggregated and compared with a single threshold, and/or otherwise processed. In preferred examples, for instance, the set of scores are aggregated (e.g., in a weighted fashion based on severity) to determine an overall score. Additionally, the set of scores is further preferably determined based on and/or compared with historical information associated with the participant, such as a set of historical scores (e.g., scores from a predetermined prior time period such as the last 1-5 weeks, a predetermined number of most recent scores, the last 1-100 scores, the last 1-50 scores, the last 1-20 scores, the last 1-10 scores, scores from the last 2-3 weeks, scores from the last 2-12 months, scores from the last month, etc.). In a set of preferred specific examples, for instance, historical scores (e.g., in each of a set of categories described above, an aggregated historical score, etc.) are weighted/scaled (e.g., based on their age) and aggregated (e.g., summed, averaged, etc.) with the current scores, wherein the aggregated scores are compared with a set of thresholds (e.g., to determine a recommendation for the participant). In some examples, an overall aggregated score is bucketed based on a set of thresholds, where the buckets can indicate, for instance, any or all of the following recommendations: that the participant receive only coaching; a low confidence that the participant receive therapy; a high confidence that the participant receive therapy; a low confidence that the participant receive psychiatry; a high confidence that the participant receive psychiatry; and/or any other recommendations, determinations, and/or predictions.

In a set of examples, S200 is performed based on a set of one or more messages from the participant.

In additional or alternative examples, S200 is performed based on other inputs (e.g., sensor data, survey data, etc.).

In a third set of variants, a set of inputs (e.g., single message, multiple messages, etc.) received in S100 is processed with multiple types of adjustment detection subsystems (e.g., in parallel, in series, in series and depending on the results of a prior adjustment detection subsystem, etc.), wherein the resulting outputs can be any or all of: individually processed (e.g., according to their own set of thresholds), aggregated, compared (e.g., to prioritize higher priority outputs), and/or otherwise utilized. In a set of specific examples, for instance each message received from the participant is processed with both a safety risk model and a clinical escalation model.

In a fourth set of variants, S200 is performed at least in part with a set of trained models and/or algorithms. In a preferred set of examples, a portion of the adjustment detection subsystem is implemented with a set of rule-based models (e.g., rule-based model which performs keyword analysis and/or supplementary word analysis and/or context analysis) to provide explainability for the outputs of the adjustment detection subsystem, while a trained model architecture is utilized for any or all of: dynamically determining a set of weights to be applied to the inputs, dynamically determining an overall set of outputs and/or recommendations based on the set of scores, and/or otherwise determining a set of outcomes. In an alternative set of examples, the entire adjustment detection subsystem is performed with a set of trained models and/or algorithms (e.g., regression model).

Additionally or alternatively, S200 can be otherwise suitably performed.

4.3 Method—Triggering an Action Based on the Set of Outputs S300

The method 200 can optionally include triggering an action based on the set of outputs S300, which functions to initiate and/or perform any or all of an escalation. This can subsequently function, for instance, to assist a participant in seeking immediate care (e.g., in an event of suicidal ideation), facilitate (e.g., automatically) a change in care associated with the participant, alert one or more users about a particular participant, and/or perform any other actions.

S300 is preferably performed in response to S200, but can additionally or alternatively be performed multiple times during the method 200 (e.g., continuously, at a predetermined frequency, in response to a trigger, etc.), in response to any other processes of the method 200, as part of and/or in parallel with any other processes of the method 200, prior to any other processes of the method 200, and/or at any other times.

The action is preferably triggered automatically (e.g., by a computing system), but can additionally or be triggered partially automatically, manually, or any combination.

The action is preferably triggered based on the set of outputs, such as based one or more scores. Additionally or alternatively, the action can be triggered based on further processing of the outputs (e.g., comparison of the set of scores with a set of thresholds, with a decision tree, with a lookup table, etc.) and/or based on any other information. In a first specific example, the method can include: in an event that all of a set of satisfaction criteria are satisfied, triggering an output at at least one of a set of interfaces, wherein the set of satisfaction criteria can include: an aggregated set of scores exceeding at least a portion of a set of thresholds and a set of inputs being absent of a set of assessments. In this example, the method can include: in an event that at least one of the satisfaction criteria is not satisfied, refraining from triggering the output. In a second specific example, the method can include: in an event that all of a set of satisfaction criteria are satisfied, determining an action operable to adjust a care plan to be automatically triggered at an interface of a set of interfaces, wherein the set of satisfaction criteria can include: the aggregated score exceeding a predetermined threshold and a set of supplementary inputs being present. In this example, the method can include: in an event that at least one of the satisfaction criteria is not satisfied, preventing the action from being automatically triggered operable to prevent adjustment of the care plan.

The action is preferably triggered at any or all of: a computing system, a hub (e.g., a coach hub, a supervisor hub, a clinician hub, a participant hub, etc.), a client application (e.g., executing a hub at a user device), a user device, and/or at any other locations.

The set of actions which can be triggered in S300 can include generating and/or triggering any number of messages, notifications, alerts, and/or other forms of communication. In some variations, for instance, triggering an action includes any or all of: contacting (e.g., messaging, calling, etc.) a user (e.g., participant, coach, supervisor, clinician, member support person, etc.); transmitting a notification to a user (e.g., participant, coach, supervisor, clinician, member support person, etc.) and/or a device of the user; establishing communication between users (e.g., between a coach and a supervisor, between a participant and a coach, between a primary coach and a backup coach, between a clinician and a participant, between a clinician and a coach, between a clinician and a supervisor, etc.) and/or user devices (e.g., automatically establishing a message thread between users); and/or any other communication actions.

In specific examples, for instance, upon predicting that the participant is experiencing suicidal ideation (e.g., based on a safety risk score exceeding a predetermined threshold), S300 can include automatically messaging information associated with suicide prevention (e.g., a telephone number for a suicide hotline, a website link for a suicide prevention website, etc.) to the participant (e.g., at the participant hub, at the participant's user device, at a mobile application executing on the participant's user device, etc.). Additionally or alternatively, S300 can include automatically initiating a call to a suicide hotline (e.g., at the hub of the participant), automatically initiating a call from the suicide hotline to the participant, automatically contacting a coach associated with the participant such that the coach can be alerted to urgently reach out to the participant, automatically contacting a backup coach associated with the participant in an event that his or her primary coach is offline, automatically contacting an emergency contact associated with the participant, and/or any other actions.

In additional or alternative specific examples, for instance, upon predicting that the participant should be escalated to clinical care (e.g., put in contact with a therapist, psychiatrist, and/or other clinician) (e.g., based on a clinical escalation prediction score exceeding a predetermined threshold), S300 can include contacting a coach associated with the participant with a message indicating that the coach should recommend to the participant that he or she should consider receiving clinical care (e.g., with a clinician associated with the digital platform, with a clinician outside of the digital platform, etc.). Additionally or alternatively, S300 can include automatically establishing communication (e.g., in a message thread) between the coach and the participant, transmitting an automated recommendation to the participant, automatically establishing communication between the participant and a clinician, automatically establishing communication between a supervisor and a coach (e.g., wherein the supervisor instructs the coach to send the recommendation to the participant), automatically establishing communication between the coach and a clinician, automatically recommending a particular clinician for the participant (e.g., to the participant, to the coach, etc.), and/or any other actions.

S300 can additionally or alternatively include preparing, annotating, and/or sending information to one or more users. In some variations, for instance, S300 includes automatically annotating (e.g., highlighting, removing sections from, etc.) messages and/or transcripts and/or other inputs associated with the platform, such as particular portions of messages and/or calls associated with the participant, wherein the annotations indicate the portions that the set of models identified as indicating a need for care adjustment (e.g., based on the set of rule-based models). In specific examples, for instance, the words and/or sentences in a participant message, and/or a set of particular messages, that resulted in the prediction scores exceeding a threshold can be highlighted and displayed to a care team member reviewing the case, thereby allowing the care team member to efficiently check that the escalation is proper (e.g., not a false positive).

S300 can additionally or alternatively include triggering an assignment of (e.g., automatically re-assigning) the participant to a particular level of care in the digital platform. This can include, for instance, automatically assigning one or more care team members (e.g., a clinical care team member in a recommended escalation) to the participant; automatically removing one or more care team members from care of the participant (e.g., removing a clinical care team member in a recommended de-escalation); assigning the participant to a different tier/level of care and/or adjusting which features of the digital platform are available to the user (e.g., increasing a frequency with which surveys are provided to the user, increasing a frequency with which check-in notifications are transmitted to the participant automatically and/or by a care team member, etc.); assigning care team members to other participants (e.g., in response to a care team member no longer being assigned to a particular participant); and/or otherwise adjusting care of the participant.

Figure 11:
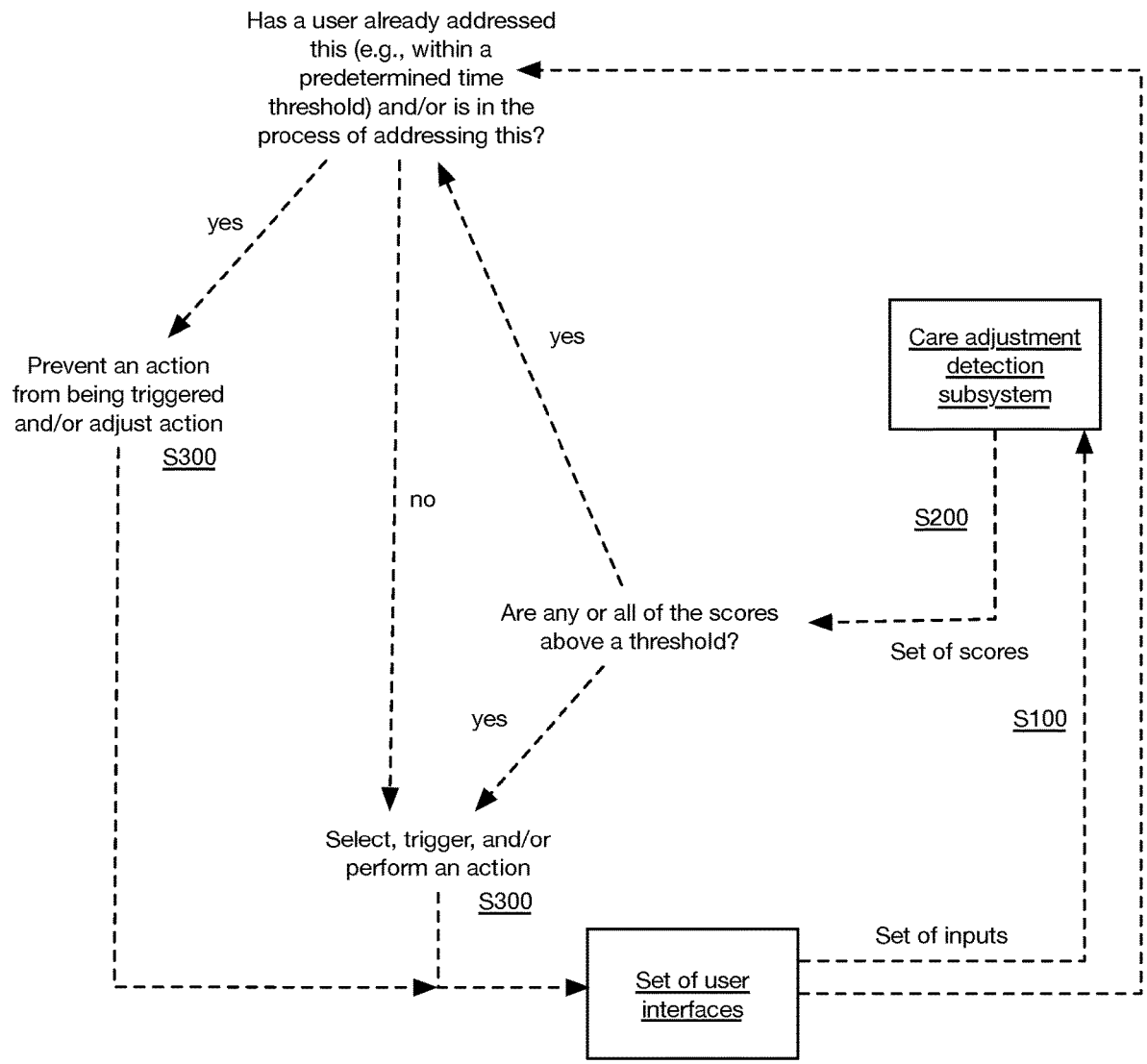
FIG. 11 is a schematic variation of a method for computer-aided care adjustment.

S300 can additionally or alternatively include (e.g., as shown in FIG. 11) preventing the triggering of an action (and/or adjusting the type and/or timing of an action), which can function to: prevent the triggering of a repeat action; prevent an unnecessary action from being triggered; prevent notification fatigue of care team members and/or participants; and/or perform any other functions.

In some variations, for instance, the types of inputs received in S100 are used (e.g., in part) to determine whether or not an action is triggered in S300 (and/or to prevent performance of any or all further processes and/or sub-processes of the method 200). For instance, in a set of examples in which an adjustment in care (e.g., escalation to clinical care, de-escalation, etc.) is recommended for the participant, the set of inputs (e.g., an indication that a care team member has already initiated and/or filled out a risk assessment for the participant, an indication that the participant is already submitting surveys at a high frequency, an indication that the participant is already seeing a clinician and/or has participated in clinical sessions, feedback from a care team member indicating that an adjustment in care is in progress, etc.) can be used to determine whether or not the adjustment for the participant is already in progress and/or has been triggered previously (e.g., within a predetermined recent time threshold), and if it has been, to prevent a repeat action (e.g., notification, automatic assignment, etc.) from being triggered and/or adjust the action that is triggered (e.g., trigger a reminder, wait a predetermined period of time before triggering, etc.).

S300 can optionally additionally or alternatively include determining and/or updating any or all of the set of models based on the set of outputs. In some variations, for instance, the set of models are continuously and/or periodically updated (e.g., retrained) based on the set of outputs and/or the outcomes (e.g., indication that a recommendation made by the adjustment detection subsystem resulted in a false positive, indication that a recommendation made by the adjustment detection subsystem resulted in a false negative, etc.) resulting from an action triggered in S300. In specific examples, for instance, any or all of the set of models are trained and updated with reinforcement learning. In additional or alternative variations, S300 includes determining, refining, and/or validating a trained model and/or a trained model which interfaces with a rule-based model. In specific examples, for instance, S300 includes determining and continuously refining a set of features and/or weights associated with a trained prediction model.

Additionally or alternatively, S300 can include any other suitable processes performed in any suitable order.

5. Variations

In a first variation of the method 200 (e.g., as shown in FIG. 4) configured to predict whether there is a safety risk present for the participant, the method 200 includes collecting a set of inputs, wherein the set of inputs can include any or all of: conversation information associated with the participant (e.g., messages between the participant and one or more coaches), surveys completed by the participant (e.g., PHQ/GAD surveys), clinical sessions (e.g., recorded calls and/or videos between the participant and a clinician, detection that a clinical session has occurred, determination of how many clinical sessions have occurred, feedback from a clinician present in the clinical session, content from the clinical session, etc.) and/or information from clinician sessions, a safety risk assessment of the coach and/or other care team members (e.g., a formal assessment of the participant's safety risk completed by a coach, coach notes regarding the participant, etc.), and/or any other inputs; processing the inputs with a safety risk model (e.g., machine learning model, combination of machine learning and rule-based models, rule-based models, etc.), wherein the model produces a safety risk prediction score; aggregating the safety risk prediction score with previous prediction scores to determine an aggregated score; and optionally triggering an action (e.g., messaging the participant a suicide hotline number, notifying a coach associated with the participant, etc.) based on the safety risk prediction score and/or the aggregated score.

Additionally or alternatively, the previous predictions can be directly analyzed at the model(s) with any or all of the other inputs and/or the method can be performed in the absence of previous prediction scores. Further additionally or alternatively, the method 200 can include any other processes.

In a second variation of the method 200 (e.g., as shown in FIG. 5) configured to predict whether a participant should be escalated to clinical care, the method 200 includes collecting a set of inputs, wherein the set of inputs can include any or all of: conversation information associated with the participant (e.g., messages between the participant and one or more coaches), surveys completed by the participant (e.g., PHQ/GAD surveys), clinical sessions (e.g., recorded calls and/or videos between the participant and a clinician) and/or information from clinician sessions, a clinical status of the participant (e.g., an indication of whether or not the participant is currently under the care of a clinician such as a therapist and/or a psychiatrist), and/or any other inputs; processing the inputs with a clinical escalation model (e.g., machine learning model, combination of machine learning and rule-based models, rule-based models, etc.), wherein the model produces a clinical escalation prediction score; aggregating the clinical escalation prediction score with previous prediction scores to determine an aggregated score; transmitting the score to a coach and/or supervisor hub; and transmitting a recommendation to a coach hub for whether or not the participant should be escalated to clinical care.

Additionally or alternatively, the previous predictions can be directly analyzed at the model(s) with any or all of the other inputs and/or the method can be performed in the absence of previous prediction scores. Further additionally or alternatively, the method 200 can include any other processes.

In a third variation, any or all of the method is performed (e.g., partially, fully, etc.) in accordance with a set of trained models and/or algorithms.

Although omitted for conciseness, the preferred embodiments include every combination and permutation of the various system components and the various method processes, wherein the method processes can be performed in any suitable order, sequentially or concurrently.

Embodiments of the system and/or method can include every combination and permutation of the various system components and the various method processes, wherein one or more instances of the method and/or processes described herein can be performed asynchronously (e.g., sequentially), contemporaneously (e.g., concurrently, in parallel, etc.), or in any other suitable order by and/or using one or more instances of the systems, elements, and/or entities described herein. Components and/or processes of the following system and/or method can be used with, in addition to, in lieu of, or otherwise integrated with all or a portion of the systems and/or methods disclosed in the applications mentioned above, each of which are incorporated in their entirety by this reference.

Additional or alternative embodiments implement the above methods and/or processing modules in non-transitory computer-readable media, storing computer-readable instructions. The instructions can be executed by computer-executable components integrated with the computer-readable medium and/or processing system. The computer-readable medium may include any suitable computer readable media such as RAMs, ROMs, flash memory, EEPROMs, optical devices (CD or DVD), hard drives, floppy drives, non-transitory computer readable media, or any suitable device. The computer-executable component can include a computing system and/or processing system (e.g., including one or more collocated or distributed, remote or local processors) connected to the non-transitory computer-readable medium, such as CPUs, GPUs, TPUS, microprocessors, or ASICs, but the instructions can alternatively or additionally be executed by any suitable dedicated hardware device.

As a person skilled in the art will recognize from the previous detailed description and from the figures and claims, modifications and changes can be made to the preferred embodiments of the invention without departing from the scope of this invention defined in the following claims.

I claim:

1. A method for computer-aided escalation of a member in a digital platform, the method comprising:
    using labeled data comprising a training message labeled with a clinical care escalation outcome, training an escalation detection subsystem using reinforcement learning to predict a score associated with the clinical care escalation outcome based on the training message, wherein the escalation detection subsystem comprises a combination of a machine learning model and a rule-based model, wherein training the escalation detection subsystem comprises learning a set of prioritization parameters;
    receiving a set of inputs from a set of interfaces of the digital platform, wherein the set of inputs comprises a message from the member;
    checking for a set of assessments associated with the member, wherein in an event that the set of assessments is present, the set of inputs further comprises the set of assessments;
    processing the message with the trained escalation detection subsystem, wherein the trained machine learning model:
        performs an adjustment of the message, wherein the adjustment comprises weighting the set of inputs using the set of learned prioritization parameters;
    and wherein the rule-based model:
        identifies a set of keywords in the adjusted message;

processes the adjusted message to determine a set of supplementary words associated with the set of keywords;

performs a set of multiple analyses based on the set of supplementary words to determine a set of contexts associated with the set of keywords;

assigning, using the escalation detection subsystem, a set of scores to the message based on the set of contexts, wherein the set of scores correspond to a clinical care escalation outcome recommendation for the member;

retrieving a historical set of scores associated with a historical set of messages from the member;

aggregating the set of scores with the historical set of scores to determine an aggregated set of scores;

comparing the aggregated set of scores with a set of thresholds;

in an event that all of a set of satisfaction criteria are satisfied, triggering an output at at least one of the set of interfaces, the set of satisfaction criteria comprising:
the aggregated set of scores exceeding at least a portion of the set of thresholds; and
the set of inputs being absent of the set of assessments;

in an event that at least one of the satisfaction criteria is not satisfied, refraining from triggering the output.

2. The method of claim 1, wherein the output is provided at an interface of a user from the set of interfaces, wherein the user is separate and distinct from the member.

3. The method of claim 2, wherein the set of interfaces comprises a first application associated with the user and a second application associated with the member, wherein the set of assessments is received from the first application and the message is received from the second application.

4. The method of claim 1, wherein the set of supplementary words is identified at least in part based on a placement of the set of supplementary words within the message relative to the set of keywords.

5. The method of claim 1, wherein the set of multiple analyses comprises at least one of:
checking for a negation of the set of keywords;
checking for an association of the member with the set of keywords; or
determining a temporal feature associated with the set of keywords.

6. The method of claim 5, further comprising decreasing a value of at least a score of the set of scores in response to at least one of:
a determination that the set of keywords is negated in the message;
a determination that the member is not associated with the set of keywords; or
a determination that the temporal feature exceeds a predetermined threshold.

7. The method of claim 1, wherein at least a portion of the set of supplementary words is separate and distinct from the set of keywords.

8. The method of claim 7, wherein the set of supplementary words comprises at least one of a modifier and a verb.

9. The method of claim 1, further comprising receiving a second set of inputs from the user, wherein the method further comprises refining a set of parameters associated with the clinical escalation detection subsystem based on the second set of inputs.

10. The method of claim 9, further comprising receiving a third set of inputs from a second member, wherein the third set of inputs comprises a second message from the second member, and processing the second message with a refined clinical escalation detection subsystem comprising the refined set of parameters.

11. The method of claim 1, wherein the machine learning model comprises a set of machine learning models, wherein a first machine learning model in the set performs the adjustment of the message and wherein a second machine learning model in the set receives and processes a set of outputs of the rule-based model, wherein the aggregated set of scores is determined at least in part with the second machine learning model.

12. The method of claim 1, further comprising downweighting the historical set of scores prior to aggregating the set of scores with the historical set of scores.

13. A non-transitory computer-readable medium storing instructions that, when executed by a computing system, cause the computing system to perform:
receiving a set of inputs from a set of interfaces of a digital platform, wherein the set of inputs comprises a message from a member of the digital platform;
checking for a set of supplementary inputs in the set of inputs, the set of supplementary inputs separate and distinct from the message;
processing the message with a trained escalation detection subsystem, wherein the trained escalation detection subsystem comprises a combination of a rule-based model, a first trained neural network, and a second trained neural network, wherein the escalation detection subsystem is trained using labeled data comprising a training message labeled with a clinical care escalation outcome, wherein the escalation detection subsystem is trained using reinforcement learning to predict a score associated with the clinical care escalation outcome based on the training message wherein the training includes learning a set of prioritization parameters;
wherein the first trained neural network:
performs a feature weighting adjustment of the message; using the set of learned prioritization parameters;
wherein the rule-based model:
identifies a set of keywords in the adjusted message;
processes the adjusted message to determine a set of supplementary words associated with the set of keywords;
performs a set of multiple analyses based on the set of supplementary words to determine a set of contexts associated with the set of keywords;
and wherein the second trained neural network:
determines a score based on the set of contexts, wherein the score corresponds to a clinical care escalation outcome recommendation for the member;
retrieving a historical score associated with a historical message from the member;
aggregating the score with the historical score to determine an aggregated score;
in an event that all of a set of satisfaction criteria are satisfied, determining an action operable to adjust a care plan for the member to be automatically triggered at an interface of the set of interfaces, the set of satisfaction criteria comprising:
the aggregated score exceeding a predetermined threshold; and
the set of supplementary inputs is present;
in an event that at least one of the satisfaction criteria is not satisfied, preventing the action from being automatically triggered operable to prevent adjustment of the care plan for the member.

14. The non-transitory computer-readable medium of claim 13, wherein the output is provided at an interface of a user from the set of interfaces, wherein the user is separate and distinct from the member.

15. The non-transitory computer-readable medium of claim 13, wherein the set of supplementary words is identified at least in part based on a placement of the set of supplementary words within the message relative to the set of keywords.

16. The non-transitory computer-readable medium of claim 13, wherein the set of multiple analyses comprises at least one of:
   checking for a negation of the set of keywords;
   checking for an association of the member with the set of keywords; or
   determining a temporal feature associated with the set of keywords.

17. The non-transitory computer-readable medium of claim 16, wherein the score is one of a set of scores, wherein the computing system further performs decreasing a value of at least a score of the set of scores in response to at least one of:
   a determination that the set of keywords is negated in the message;
   a determination that the member is not associated with the set of keywords; or
   a determination that the temporal feature exceeds a predetermined threshold.

18. The non-transitory computer-readable medium of claim 17, wherein the set of supplementary words comprises at least one of a modifier and a verb.

* * * * *